United States Patent [19]
Albrecht et al.

[11] Patent Number: 6,047,206
[45] Date of Patent: Apr. 4, 2000

[54] GENERATION OF LOCALIZED CARDIAC MEASURES

[75] Inventors: Paul Albrecht, Bedford; Jeffery M. Arnold, Wellesley; Richard J. Cohen, Waban; Paul Lander, Lincoln, all of Mass.

[73] Assignee: Cambridge Heart, Inc., Bedford, Mass.

[21] Appl. No.: 08/895,808

[22] Filed: Jul. 17, 1997

Related U.S. Application Data

[60] Provisional application No. 60/021,918, Jul. 17, 1996.

[51] Int. Cl.[7] .................................................. A61B 5/0402
[52] U.S. Cl. .............................................................. 600/509
[58] Field of Search .................................. 600/508, 507, 600/515, 518

[56] References Cited

U.S. PATENT DOCUMENTS

| | | |
|---|---|---|
| 4,082,087 | 4/1978 | Howson . |
| 4,084,583 | 4/1978 | Hjort . |
| 4,422,459 | 12/1983 | Simson . |
| 4,458,691 | 7/1984 | Netravali . |
| 4,458,692 | 7/1984 | Simson . |
| 4,492,235 | 1/1985 | Sitrick . |
| 4,622,980 | 11/1986 | Kunig . |
| 4,630,204 | 12/1986 | Mortara . |
| 4,732,157 | 3/1988 | Kaplan et al. . |
| 4,751,931 | 6/1988 | Briller et al. . |
| 4,760,540 | 7/1988 | Yuen . |
| 4,781,201 | 11/1988 | Wright et al. . |
| 4,783,660 | 11/1988 | Pierce . |
| 4,793,361 | 12/1988 | DuFault . |
| 4,802,491 | 2/1989 | Cohen et al. . |
| 4,807,173 | 2/1989 | Sommen et al. . |
| 4,917,099 | 4/1990 | Stice . |
| 4,974,598 | 12/1990 | John . |
| 4,979,110 | 12/1990 | Albrecht et al. . |
| 4,993,423 | 2/1991 | Stice . |
| 5,010,888 | 4/1991 | Jadvar et al. . |
| 5,020,540 | 6/1991 | Chamoun ............................. 600/515 |
| 5,020,541 | 6/1991 | Marriott . |
| 5,046,504 | 9/1991 | Albert et al. . |
| 5,054,496 | 10/1991 | Wen et al. ............................. 600/509 |
| 5,107,849 | 4/1992 | Bellin et al. . |
| 5,109,862 | 5/1992 | Kelen et al. . |
| 5,146,926 | 9/1992 | Cohen . |
| 5,148,812 | 9/1992 | Verrier et al. . |

(List continued on next page.)

OTHER PUBLICATIONS

P. Lander et al., "Principles and signal processing techniques of the high–resolution electrocardiogram," Progress in Cardiovascular Disease 35:169–188 (1982).

R. Plonsey, "Laws governing current flow in the volume conductor" in the Theoretical Basis of Electrocariography, C. V. Nelson and D.B. Geselowitz, Eds., Clarendon Press, Oxford pp. 165–174, 1996.

M.L. Simoons et al. "Online Processing of Orthogonal Exercise Electrocardiograms" Computers and Biomedical Research 8:105–117, 1995.

J.C. Davis, Statistics and Data Analysis in Geology, 2nd Edition (1996) pp. 383–405.

Adam et al., "Ventricular Fibrillation and Fluctuations in the Magnitude of the Repolarization Vector," Computers in Cardiology, pp. 241–244 (1982).

Adam et al., "Fluctuations in T–Wave Morphology and Susceptibility to Ventricular Fibrillation," J. Electrocardiology 17(3), pp. 209–218 (1984).

(List continued on next page.)

*Primary Examiner*—Jeffrey R. Jastrzab
*Assistant Examiner*—George R. Evanisko
*Attorney, Agent, or Firm*—Fish & Richardson P.C.

[57] ABSTRACT

A subject suspected of experiencing a myocardial infarction is monitored by applying sensors to the subject, where the sensors are configured to produce electrical signals representative of cardiac activity of the subject. Electrical signals are received from at least two of the sensors. The received signals then are processed to obtain a localized cardiac measure that is analyzed to determine whether the subject is experiencing a myocardial infarction.

37 Claims, 16 Drawing Sheets

U.S. PATENT DOCUMENTS

| | | |
|---|---|---|
| 5,188,116 | 2/1993 | Pommrehn et al. . |
| 5,234,404 | 8/1993 | Tuttle et al. . |
| 5,237,995 | 8/1993 | Cano . |
| 5,265,617 | 11/1993 | Verrier et al. . |
| 5,318,037 | 6/1994 | Evans et al. . |
| 5,323,783 | 6/1994 | Henkin et al. . |
| 5,341,811 | 8/1994 | Cano . |
| 5,348,020 | 9/1994 | Hutson . |
| 5,377,687 | 1/1995 | Evans et al. . |
| 5,419,337 | 5/1995 | Dempsey et al. ........................ 600/515 |
| 5,421,342 | 6/1995 | Mortara . |
| 5,437,285 | 8/1995 | Verrier et al. . |
| 5,469,857 | 11/1995 | Laurent et al. . |
| 5,520,191 | 5/1996 | Karlsson et al. . |
| 5,520,683 | 5/1996 | Subramaniam et al. . |
| 5,560,370 | 10/1996 | Verrier et al. . |
| 5,570,696 | 11/1996 | Arnold et al. . |

OTHER PUBLICATIONS

Adam et al., "Estimation of Ventricular Vulnerability to Fibrillation Through T–Wave Time Series Analysis," Computers in Cardiology, pp. 307–310 (1981).

Cano et al., "Enhancement of Low—Level ECG Component in Noise With Time—Sequenced Adaptive Filtering," J. Electrocardiology, Vol. 23 Supplement, pp. 176–183 (1990).

Changiu et al., "A New Algorithm for Adaptive Nosie Cancellation Using Singular Value Decomposition," Acta Automatica Sinica, vol. 12, No. 2, pp. 146–153 (Apr. 1986) (Engl. translation and original paper).

Damen et al., "The use of the Singular Value Decomposition in Electrocardiology, " Medical & Biological Engineering & Computing, pp. 473–482 (1982).

El–Sherif et al., "Beat–to–Beat High–Resolution Electrocardiology; Technical and Clinical Aspects," Progress in Cardiovascular Diseases, vol. XXXV, No. 6, pp. 407–415 (1993).

El–Sherif et al., "Appraisal of a Low Noise Electrocardiogram," J. Am. Coll. Cardiol. 1(2), pp. 456–467 (1983).

Evans et al., "Redundancy Reduction for Improved Display and Analysis of Body Surface Potential Maps," Circulation Research, vol. 49, No. 1, pp. 197–203 (1981).

Kaufer et al., "Optimization of Multi–Ring Sensing Electrode Set," Annual International Conference of the IEEE Engineering in Medicine and Biology Society, vol. 12, No. 2, pp. 0612–0613 (1990).

Lander et al., "Relation Between Estimates of Myocardial Ischemia Using High Resolution Electrocardiography and Scintigraphic Images".

Meyer et al., "Electrocardiogram Baseline Noise Estimation and Removal Using Cubic Splines and State–Space Computation Techniques," Computers and Biomedical Research 10, pp. 459–470 (1977).

Mortara, "Source Consistency Filtering –Application to Resting ECG's," J. Electrocardiology, vol. 25 Supplement, pp. 200–206 (1992).

Mortara, "Source Consistency Filtering —A New Tool for ECG Noise Reduction," IEEE, pp. 125–128 (1992).

Nearing et al., "Dynamic Tracking of Cardiac Vulnerability by Complex Demodulation of the T Wave," Science, vol. 252, pp. 437–440 (1991).

Nearing et al., "Personal Computer System for Tracking Cardiac Vulnerability by Complex Demodulation of the T Wave," J. Appl. Physiol. 74, pp. 2606–2612 (1993).

Pedretti et al., "Prediction of Late Arrhythmic Events After Acute Myocardial Infarcation . . . Sustained Monomorphic Ventricular Tachycardia," A. J. Cardiol., vol. 71, No. 13, pp. 1131–1141 (1993).

Rasquinha et al., "Directional Depolarization Sensors of Body Surface ECG," Annual International Conference of the IEEE Engineering in Medicine and Biology Society, vol. 13, No. 4, pp. 1680–1681 (1991).

Ring et al., "Exercise–Induced ST Segment Alternans," American Heart Journal, vol. 111, No. 5, pp. 1009–1011 (1986).

Salerno et al., "Ventricular Arrhythmias During Acute Myocardial Ischaemia in Man. The Role and Significance of R–ST–T Alternans . . . ," European Heart Journal 7 (Supp. A), pp. 63–75 (1986).

Shvartsman et al., "Multichannel Signal Processing Based on Logic Averaging," IEEE Transactions on Biomedical Engineering, vol. BME–29, No. 7, pp. 531–536 (1982).

Smith et al., "Electrical Alternans and Cardiac Electrical Instability," Circulation, vol. 77, No. 1, 110–121 (1988).

Smith et al., "Subtle Alternating Electrocardiographic Morphology as an Indicator of Decreased Cardiac Electrical Stability," Computers in Cardiology, pp. 109–112 (1985).

Smith, "The Stochastic Nature of Cardiac Electrical Instability: Theory and Experiment," thesis, Mass. Institute of Technology (1985).

Verrier et al., "Electrophysiologic Basis for T Wave Alternans as an Index of Vulnerability to Ventricular Fibrillation," J. Cardiovascular Electrophysiology, vol. 5, No. 5, pp. 445–461 (1994).

Wel et al., "A New Method for Reducing Signal–Overlapping Noise in Standard Electrocardiogram," Proceedings of Computers in Cardiology, pp. 795–797 (1993).

Widrow, "Adaptive Interface Canceling," Adaptive Signal Processing, Applications Part IV, Chap. 12, Prentice–Hall, Englewood Cliffs, NJ, pp. 302–367 (1985).

Zareba et al., "T Wave Alternans," J. Am. Coll. Cardiol., vol. 23, pp. 1541–1546 (1994).

Zimmerman et al., "Beat–to–Beat Detection of Ventricular Late Potentials with High–Resolution Electrocardiography," American Heart Journal, vol. 121, No. 2, Part 1, pp. 576–585 (1991).

GENERATION OF LOCALIZED CARDIAC MEASURES

CROSS REFERENCE TO RELATED APPLICATIONS

This application claims priority from U.S. Provisional Application No. 60/021,918, entitled "IMPROVED ASSESSMENT OF CARDIAC FUNCTION" and filed Jul. 17, 1996, which is incorporated by reference.

BACKGROUND

The invention relates to the generation of localized cardiac measures.

Electrical activity of the heart generates an electrical potential on the body surface. At any given location on the body, this potential includes contributions from every region of the heart, with the contribution from a particular region being inversely proportional to the square of the distance from the region to the location on the body. Given the anatomy of the heart and chest, the potentials at most locations on the body surface represent summed electrical activity from a large region of the heart.

The body surface electrocardiogram (ECG) is a measure of electrical activity of the heart. The ECG provides a measure of the potential difference between two points on the body surface as a continuous function of time. The ECG is routinely measured using standard ECG electrodes. Commonly, ten electrodes are used, four of which are near the limbs and six of which span the chest, primarily on the left side. The signals recorded from these electrodes are processed to form a standard set of twelve ECG leads.

Each of the standard twelve ECG leads represents the difference between signals from two sensors that are located a significant distance from one another. Standard leads I, II and III represent the difference between pairs of the limb electrodes. They are referred to as bipolar leads because they represent the difference of two electrodes. Standard leads AVR, AVL, AVF and V1–V6 represent the difference between an electrode and Wilson's central terminal, a reference created by averaging three of the limb electrodes. Leads referenced to Wilson's central terminal are referred to as unipolar leads. Standard electrocardiogram leads, such as the unipolar leads, do not represent localized electrocardiogram signals.

SUMMARY

The invention provides techniques for generating localized cardiac measures for use in detecting a myocardial infarction (i.e., a heart attack).

Every year, just in the United States, more than a million people experience a myocardial infarction. In general, an acute, evolving myocardial infarction may be suspected when a patient appears in an emergency room with symptoms, such as chest pain, dizziness or malaise. Such an infarction results from the closing of one or more major arteries due to severe coronary artery disease.

Closing of a coronary artery results in myocardial ischemia (i.e., reduced myocardial blood flow) that, if left untreated, may result in scarring of the myocardial tissue. Both of these effects result in localized changes in heart function due to localized changes in myocardial blood flow, and, in some instances, may result in global changes in heart function. These localized changes may result in ischemically-altered electrical activity in the heart. However, if the changes are highly localized in the heart, the ischemically-altered electrical activity may make an insignificant contribution to a body surface potential distribution sensed by conventional unipolar leads. The altered electrical activity may be detected by monitoring localized cardiac measures to provide an early, accurate diagnosis of myocardial infarction. A localized cardiac measure is defined as a cardiac measure generated using signals produced by two or more sensors, or electrodes, that are spaced by a distance less than the spacing between sensors used to produce standard electrocardiogram leads. In general, a localized cardiac measure involves signals from sensors that are spaced by less than three inches, and that may be spaced by an inch or less.

It is important to make the diagnosis of myocardial infarction as quickly as possible. For example, the effectiveness of thrombolytic therapy, which thins the blood and reopens the blocked artery, decreases as the delay in administering the therapy increases. If blood flow is restored in the heart (i.e., if revascularization occurs), the electrical, chemical and mechanical changes brought about by restricted oxygen supply due to myocardial ischemia may revert to a normal condition. Without revascularization, myocardial cells associated with an ischemic condition will eventually die and form scar tissue. Scar tissue is electrically inactive, does not contract, and, therefore, does not contribute to the mechanical pumping action of the heart. Reduced mechanical efficiency of the heart due to scar tissue and electrical instability of heart muscle in regions bordering the scar tissue are causes of morbidity and mortality following a heart attack.

Thrombolytic therapy has been effective in limiting damage to heart tissue during a heart attack. It is most effective if administered in the first hour following the onset of symptoms. The benefit of the therapy is still significant if thrombolytics are administered within four hours of the onset of symptoms. Presently, the standard twelve-lead ECG is the diagnostic test most readily available in the emergency room setting. However, abnormal indications in the twelve-lead ECG occur in only 60% of patients with acute myocardial infarctions. The likelihood of an abnormal ECG increases with time, as there is a continuous process of transition from ischemic tissue (tissue deprived of oxygen) to infarcted tissue (tissue that has died, formed scar tissue, and is not recoverable). In general, the standard ECG does not detect this transition.

During a myocardial infarction, the body manufactures certain enzymes which can be detected in the blood. However, definitive enzyme-based tests for the presence of acute myocardial infarction generally are not available until about six hours after the onset of symptoms, which is too late to guide thrombolytic therapy.

The invention promises to provide a sensitive, early indicator of an acute myocardial infarction. The techniques of the invention also may be used to identify the blocked artery or arteries, and to track the progression of an evolving myocardial infarction, with respect to factors such as the transition from ischemia to scarring, the degree of scarring, and the efficacy of thrombolysis or other treatments.

In one aspect, generally, the invention features monitoring a subject suspected of experiencing a myocardial infarction. Sensors are applied to the subject. The sensors are configured to produce electrical signals representative of cardiac activity of the subject. Electrical signals are received from at least two of the sensors, and are processed to obtain a localized cardiac measure. The localized cardiac measure then is analyzed to determine whether the subject is experiencing a myocardial infarction.

Embodiments of the invention may include one or more of the following features. Analyzing the localized cardiac measure may include analyzing a temporal trend in the localized cardiac measure. The localized cardiac measure may be a localized measure of myocardial ischemia, and may be produced from a single localized ECG, or from multiple localized ECGs recorded from several locations on the body.

The localized ECG is created from signals of two electrodes that are close to each other. Unlike standard ECGs, localized ECGs from proximal electrodes accentuate the activity of regions of the heart which are close to the electrodes. Regions which are significantly farther from the electrodes than the spacing between the electrodes create a common contribution that may be eliminated by generating a signal that represents the difference between the signals produced by the two electrodes.

The temporal trend may be based on ST segment changes in a localized ECG. This determination may include computing a normalized value of ST segment changes, and also may include computing characteristics of a body surface spatial distribution of ST segment changes. By mapping areas of the torso, the spatial distribution of the localized ECG provides information about localized changes in small regions of the heart.

One example of a localized ECG is the second derivative of the surface potential distribution (i.e., the spatial derivative), referred to as the Laplacian ECG. Measurements of the spatial derivative, such as the Laplacian ECG, may reflect local activity in discrete regions of the heart.

The recorded localized electrocardiograms may have a low signal-to-noise ratio due to the low amplitude of the localized electrocardiogram. A signal-to-noise characteristic of the localized cardiac measure may be enhanced. For example, an averaging process based on a measure of statistical central tendency of the localized cardiac measure may be used to enhance the signal-to-noise characteristic. The averaging process may include, for example, ensemble averaging or median averaging. The signals may be processed to remove baseline noise using an impedance signal estimate.

The localized cardiac measure may be normalized using a parameter computed, for example, from standard or localized ECGs. For example, the localized cardiac measure may be normalized through multiplication by a scale factor computed from standard or localized ECGs.

The localized cardiac measure may be generated by combining measures from multiple signals, and this composite measure may be analyzed to detect myocardial ischemia. This analysis may include visual interpretation of a spatial display of the localized cardiac measure, or of a graphical representation of a parameter of the localized cardiac measure.

The sensors may be implemented using special, multi-segment electrodes. These electrodes are made mechanically flexible to reduce movement artifacts. The geometry of the segments is designed to make the electrode resistant to sweat or other moisture to prevent short circuiting of the segments. The adhesiveness of the electrodes is further protection against poor electrical contact between the electrode sensing elements and the skin. The segment geometry is further designed to minimize differential impedances between the sensing element-skin interfaces of the segments. The electrode is also able to sink and source impedance signals at each segment. These impedance signals are used to sense variations in the localized ECG caused by movement or impedance differences in the sensing element-skin interfaces. The impedance signals are then used to attenuate baseline variations in the ECG.

The localized cardiac measure may be an approximation to a body surface spatial differential of an ECG. For example, it may be an approximation to a body surface Laplacian. The localized ECG may more generally be a spatially-high-pass-filtered body surface potential. Generation of the localized cardiac measure may include reconstruction of a standard ECG, such as a standard twelve-lead ECG, by transformation of the signals recorded from the sensors.

A display of the temporal trend in localized cardiac measure may be presented. The display may include a representation of a standard ECG. When the localized cardiac measure is obtained at multiple locations, the display may include a map, such as an isometric map, a contour map, a gray scale map, a color map, an isopotential map, or an isochronous map. The map, which may be a polar image map, also may use colors to represent ranges of values of the localized cardiac measures in different areas that correspond approximately to areas of the body surface.

The display may include a graphical representation of the cardiac measure at positions corresponding to locations of the sensors. For example, the display may be a graphical image with superimposed cardiac measures. The display also may be a plot of a time-dependence of a quantity derived from the localized cardiac measure.

Generation of the map may include estimating the localized cardiac measure at locations other than the locations of the recorded signals. Estimating may include computing an array of values of the localized cardiac measure. The array may correspond to the spatial distribution of the localized cardiac measures, and may present an interpolated regular grid with no missing values. The spatial distribution may be computed by kriging. The array also may be computed using two-dimensional filtering, smoothing or spatial differentiation.

For mapping, a large number (e.g., 8 to 512) of electrodes may be placed on the patient's torso. Coverage of the anterior, lateral or posterior parts of the torso is achieved with electrodes placed approximately regularly from each other. A potential of particular interest, for example the potential at the J point (a point defined as the end of the QRS complex) is measured in each ECG waveform. An isopotential map is computed from the distribution of values on the body surface and then displayed.

Placement of a large number of closely-spaced unipolar electrodes generates a two-dimensional representation of the surface potential that varies smoothly between recording sites. In contrast, the Laplacian ECG can exhibit abrupt local changes due to the localizing nature of the Laplacian ECG. The Laplacian ECG changes the weighting of distributed cardiac sources, emphasizing those that are most proximal to the sensing electrode.

The standard ECG recorded during stress will not be able to detect regional changes in cardiac activity. By mapping areas of the torso, the spatial distribution of the localized ECG provides heretofore unavailable information about localized changes in small regions of the heart.

In another aspect, generally, the invention features monitoring a subject for naturally occurring myocardial ischemia that occurs during the subject's routine daily activity. Naturally occurring ischemia usually is precipitated by events such as emotional or physical exertion. Ischemia during routine daily activity may lead eventually to myocardial infarction. Sensors configured to produce electrical signals representative of cardiac activity are applied to a subject and electrical signals from at least two of the sensors are received. The received signals then are processed to obtain a localized cardiac measure that is analyzed to assess whether the subject is experiencing naturally occurring myocardial ischemia. Analyzing the localized cardiac measure may include analyzing a temporal trend of a measure of myocardial ischemia. When the localized cardiac measure is a localized electrocardiogram, analyzing the localized electrocardiogram may include analyzing an ST segment of the localized electrocardiogram. The electrical signals may be received at a portable recording device.

In other aspects, the invention features assessing spatial variation of a localized cardiac measure. Sensors configured to produce electrical signals representative of cardiac activity are applied to a subject and electrical signals from at least two of the sensors are received. The signals are processed to obtain a localized cardiac measure at at least two locations. The spatial variation of the localized cardiac measures then is determined.

In other aspects, the invention features assessing QT dispersion, assessing atrial activity, or detecting late potentials in cardiac activity of a subject. Sensors configured to produce electrical signals representative of cardiac activity are applied to a subject and electrical signals from at least two of the sensors are received. The signals are processed to obtain a localized cardiac measure that is used to assess QT dispersion or atrial activity, or to detect late potentials in cardiac activity of the subject. Atrial activity may include the timing of P-waves in an electrocardiogram.

In another aspect, the invention features determining whether a wide complex tachycardia in cardiac activity of a subject is ventricular or supraventricular in nature. Electrical signals representative of cardiac activity of a subject are received and processed to obtain a localized cardiac measure of wide complex tachycardia. The localized cardiac measure then is used to determine whether the wide complex tachycardia is ventricular or supraventricular in origin.

Other features and advantages of the invention will become apparent from the following description, including the drawings, and from the claims.

DESCRIPTION

Figure 1:
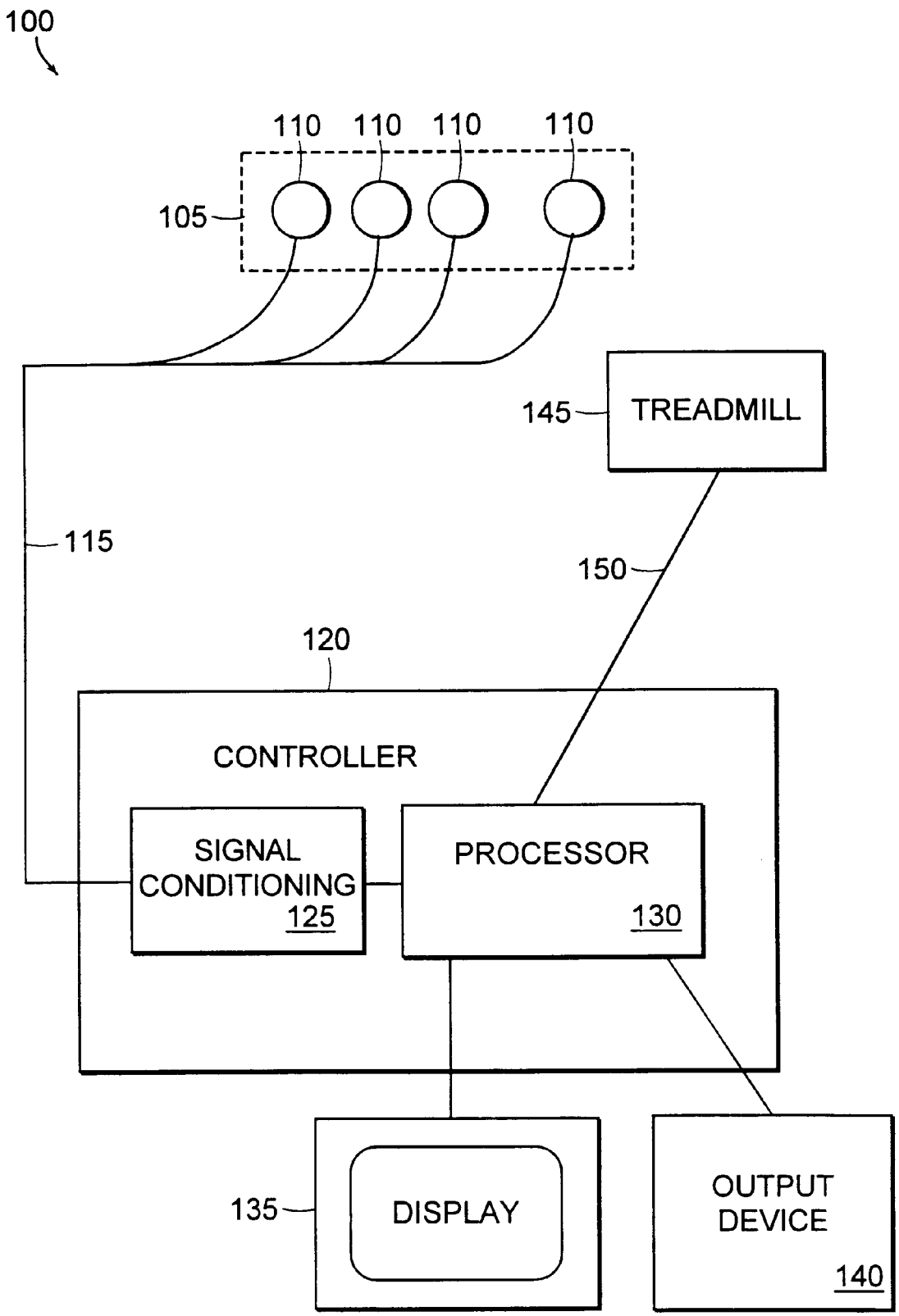
FIG. 1 is a block diagram of an ECG system.

Referring to FIG. 1, an ECG system 100 includes an array 105 of electrodes 110 that are applied to cover the anterior, lateral and posterior areas of the torso. The electrodes function separately from one another, but may be physically affixed together to form a flexible band or other arrangement. The system 100 further includes a set of leads 115 that connect the electrodes to a system controller 120. The controller includes signal conditioning circuitry 125 and a processor 130. The circuitry 125 receives analog signals from the leads 115 and provides conditioned digital signals to the processor 130. The processor 130 processes the conditioned signals to produce results that the processor then provides to a connected display 135 or to an output device 140, such as a printer. The processor may optionally control physiologic stress of the patient's heart by controlling an exercise device, such as a treadmill 145 having programmable slope and walking speed, through control signals supplied via a lead 150.

The system 100 may be used to measure myocardial ischemia during physiologic stressing of a subject's heart. The system also may be used to monitor a subject suspected of experiencing a myocardial infarction (i.e., a heart attack).

Figure 2:
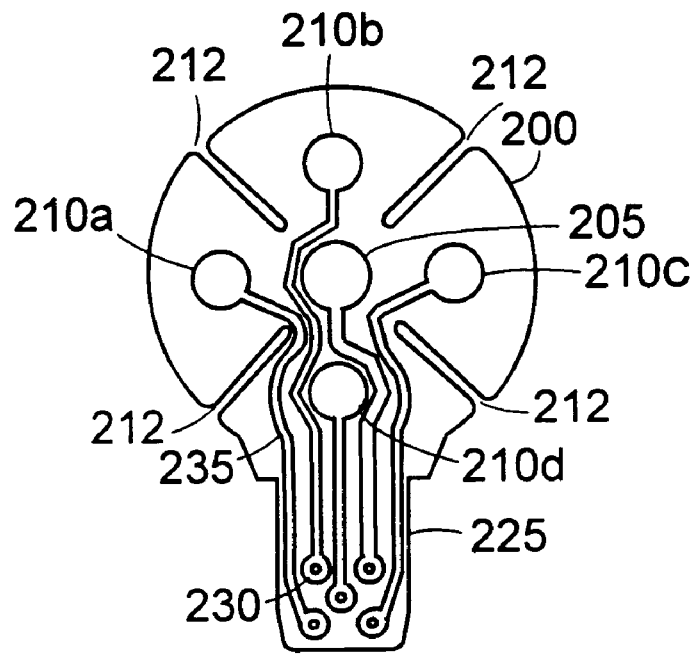
FIG. 2 is a top view of an electrode and a connector assembly of the system of FIG. 1.
Figure 2:
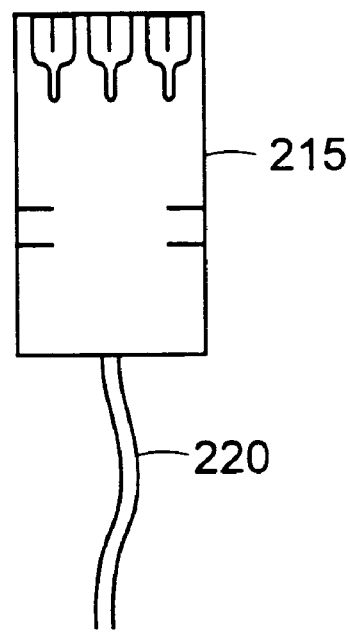

Referring to FIG. 2, each electrode 110 may be a multi-segment electrode 200 that includes a center segment 205 and four exterior segments 210a, 210b, 210c and 210d that together surround the center segment 205. The position of the center segment 205 corresponds to the average of the positions of the exterior segments 210a, 210b, 210c and 210d. The diameter of the region defined by the exterior segments is on the order of 1 to 3 inches.

Cutouts 212 along the circumference of the electrode 200 provide flexibility to the electrode. This lessens mechanical distortion due to patient movement. Such mechanical distortion has been found to change the impedance of an electrode and thereby affect the signals produced by the electrode.

The multi-segment electrode 200 is configured for use with a connector 215 that is attached to a lead 220. To this end, the electrode 200 includes a connection tail 225. The connection tail 225 includes five connection holes 230 for attachment to the connector 215. Four of the connection holes 230 are arranged in a square configuration, with a fifth connection hole being located in the center of the square. Each hole 230 passes through an extension 235, or trace, of a segment of the electrode 200. The construction and operation of a connector comparable to the connector 215 is discussed in detail in U.S. application Ser. No. 08/724,885, entitled "ELECTRODE CONNECTOR" and filed Oct. 3, 1996, which is incorporated by reference.

Figure 3:
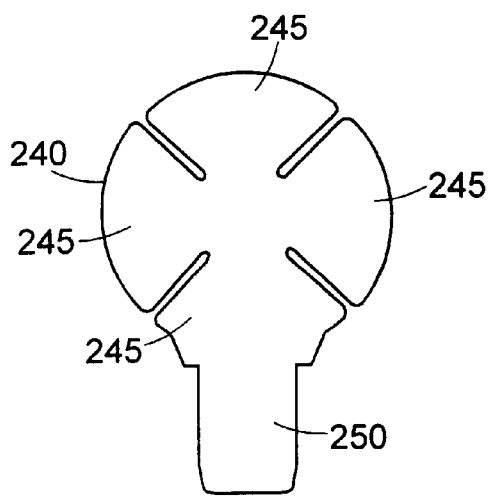
FIGS. 3–6 are bottom views of the electrode of FIG. 2 during different stages of construction of that electrode.

Referring to FIG. 3, the multi-segment electrode 200 is formed on a basepad 240. The basepad is made from an insulating, flexible film, such as a polyester film. The basepad 240 is shaped to include a section 245 corresponding to each segment of the electrode and a section 250 corresponding to the connection tail 225.

Figure 4:
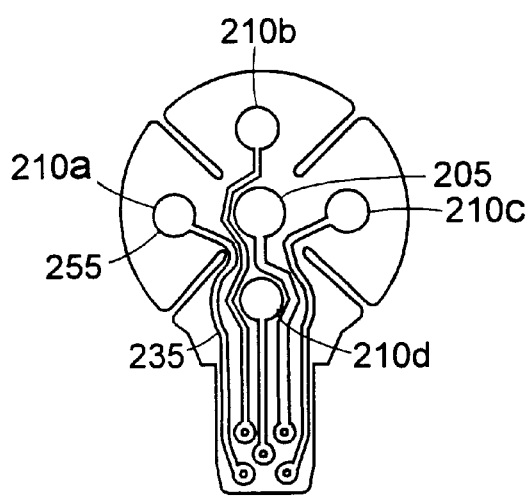
Figure 5:
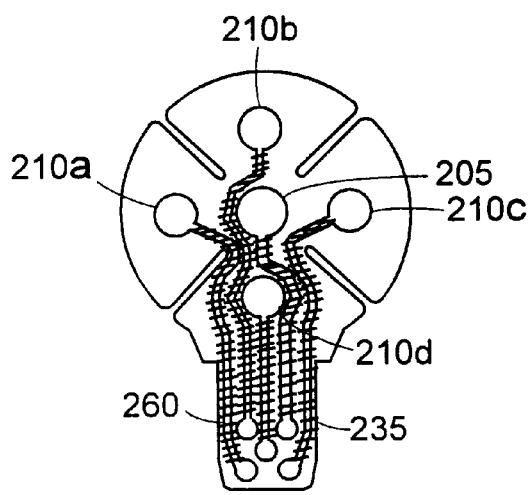

As shown in FIG. 4, the segments 205, 210a, 210b, 210c and 210d are formed by printing on the surface of the basepad 240 with a conductive material 255, such as silver-chloride ink. The extensions 235 are formed in the same manner. Next, as shown in FIG. 5, a layer of insulating material 260 is deposited on the silver-chloride ink 255 that defines the extensions 235. With the exception of portions of the extensions that will be adjacent to the holes 230, the insulating material covers the entire surface area of the extensions.

Figure 6:
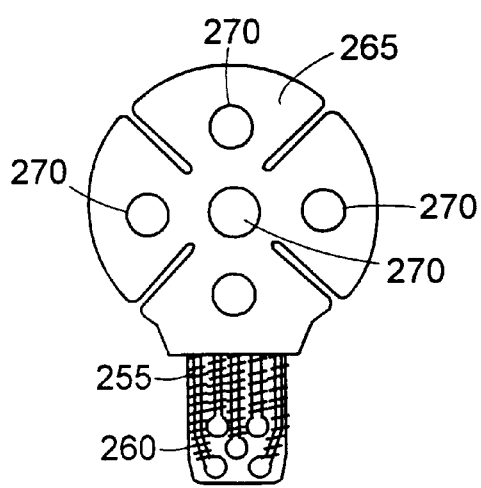
Figure 7:
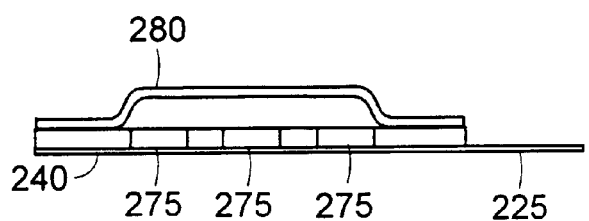
FIG. 7 is a side view of the electrode of FIG. 2.

Referring to FIG. 6, a layer of plastic flexible foam 265 is attached to the section 245 of the basepad 240 corresponding to the segments of the electrode. The foam is positioned on top of the silver-chloride ink 255 and the insulating material 260 so that the ink and the insulating material are sandwiched between the foam and the basepad. The foam includes holes 270 that correspond to the electrode segments 205, 210a, 210b, 210c and 210d. The holes form wells that hold electrically conductive gel 275 (FIG. 7). The gel 275 provides a conductive path from the patient's skin to the silver-chloride ink that defines each electrode segment.

The connection holes 230 in the connection tail 225 are formed through the basepad 240 and the silver-chloride ink to produce the electrode 200 illustrated in FIG. 2. Referring to FIG. 7, in storage and prior to use, a cover 280 is attached to the adhesive surface of the foam 265 to keep the electrode clean prior to use and to prevent the conductive gel 275 from drying.

Figure 8:
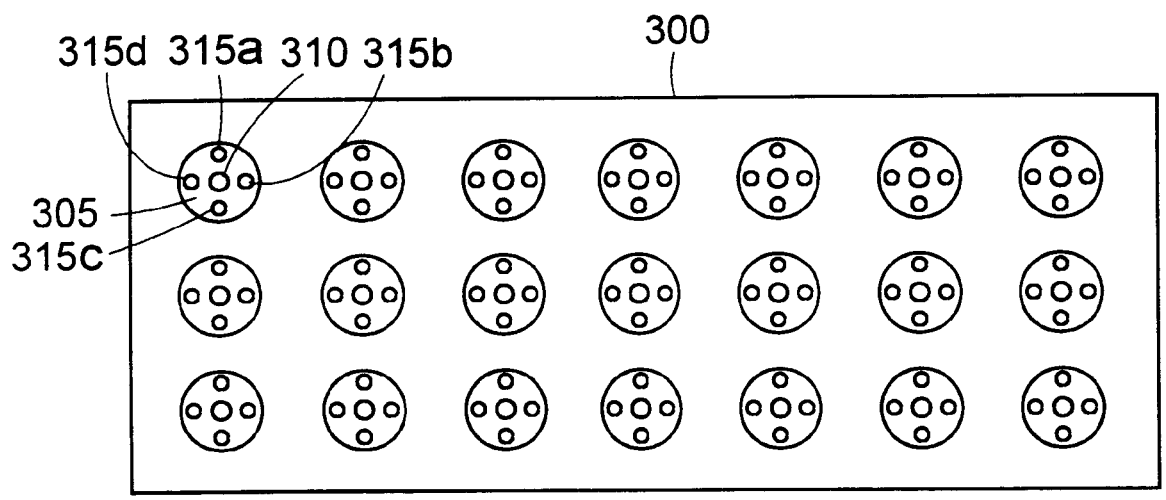
FIG. 8 is a top view of a band of electrodes.

Referring to FIG. 8, the array 105 of electrodes 110 also may be implemented as a band 300 of electrodes 305. Similarly to the electrodes 200, each electrode 305 is a multi-segment electrode that includes a center segment 310 and four arcuate exterior segments 315a, 315b, 315c and 315d that together surround the center segment 310. The position of the center segment 310 corresponds to the average of the positions of the exterior segments 315a, 315b, 315c and 315d (i.e., the center segment 310 is centered relative to the exterior segments 315a–315d. As with the electrode 200, the diameter of the region defined by the exterior segments is on the order of 2 and ⅛ inches. Use of the band 300 provides for ease of application and ensures that there is consistent spacing between the electrodes.

Figure 9:
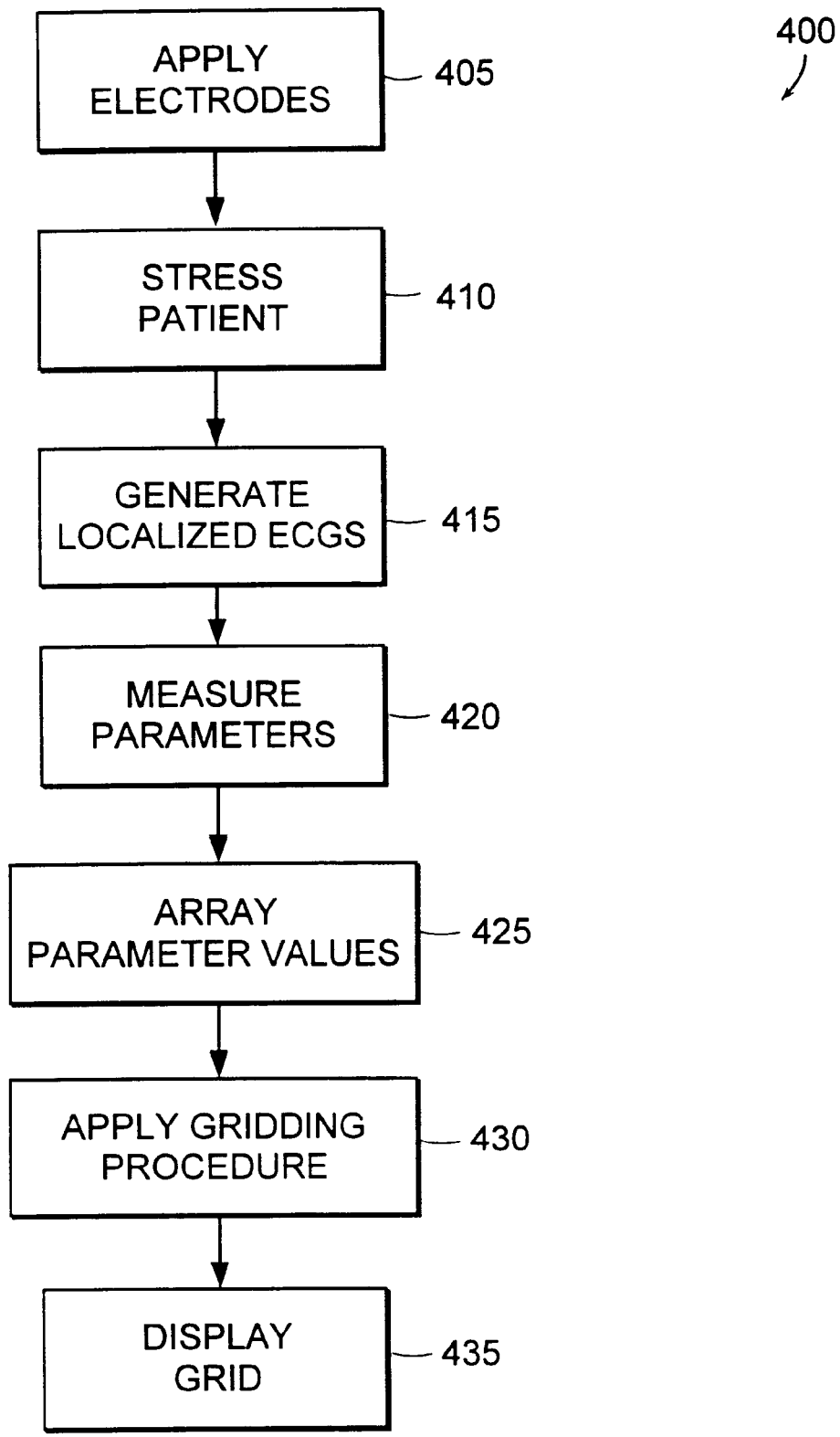
FIG. 9 is a flow chart of a procedure for measuring myocardial ischemia.

Referring to FIG. 9, the system 100 may be used to detect myocardial ischemia according to a procedure 400. Initially, the electrodes are applied to the torso (step 405). Coverage of the electrodes extends vertically from just below the clavicle to the bottom of the rib cage and horizontally from the anterior right mid-clavicular line to the posterior left mid-clavicular line. The electrodes may be applied as individual electrodes 200 (FIG. 2) or as a belt of electrodes 300 (FIG. 8).

Once the electrodes have been applied to the torso, the patient's heart is stressed physiologically using a controlled protocol (step 410). The protocol may consist either of exercise or of pharmacological stress testing. For example, the patient may be exercised using the treadmill 145. Alternatives to the treadmill, such as climbing and bicycle ergometers, also may be used. In general, the stress protocol may have several stages, including control and warm-up stages, stages featuring progressively heavier stress, a relaxation stage, and a recording stage occurring between fifteen minutes and twenty four hours after the test. Recording of ECG signals may take place during any or all of these stages.

Figure 10:
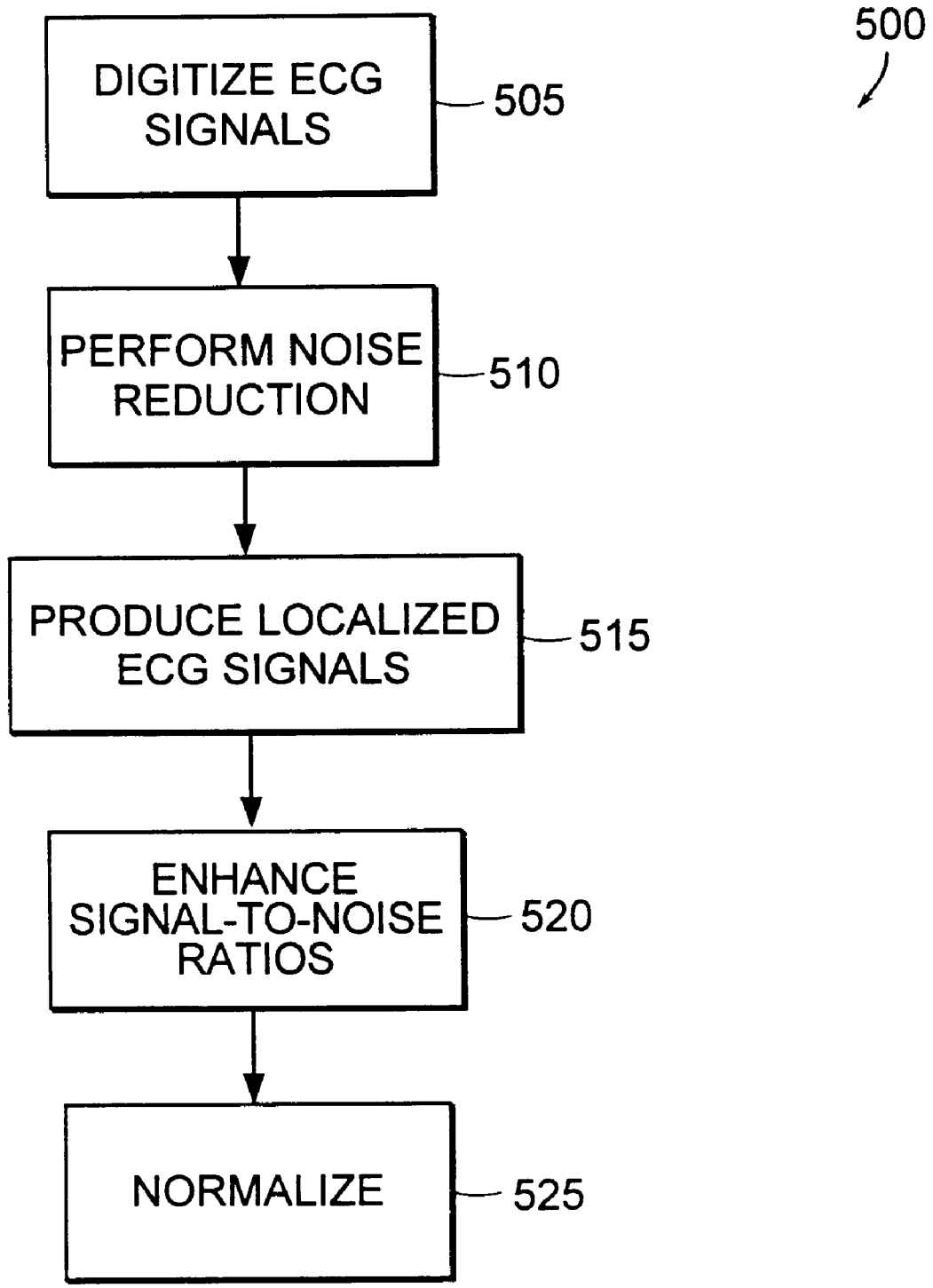
FIG. 10 is a flow chart of a procedure for processing ECG signals.

When ECG signals are recorded, the processor generates a set of localized ECG signals (step 415). As shown in FIG. 10, the processor may generate the localized ECG signals according to a procedure 500. Initially, the ECG signals are digitized by the signal conditioning circuitry 125 (step 505). Digitizing the signals prior to generating the localized ECG signals allows signals from different segments to be weighted in a flexible way, depending on their geometry or location, and permits an impedance measurement, produced from one or more electrodes or electrode segments, to be used with the ECG signals to remove baseline noise. Localized ECG signals also may be generated by combining analog signals recorded from individual sensing elements of the electrodes or electrode segments prior to digitizing those signals.

Next, ECG baseline wander noise introduced by, for example, patient motion or respiration, or heart movement, is removed using impedance measures recorded from one or more electrodes (step 510). Use of impedance measures and other techniques for reducing noise in ECG signals are described in U.S. application Ser. No. 08/557,883, entitled "USING RELATED SIGNALS TO REDUCE ECG NOISE" and filed Nov. 14, 1995, which is incorporated by reference.

The localized ECG signals then are produced from the noise-reduced ECG signals (step 515). Each localized ECG signal corresponds to an approximation of the surface differential signal, also known as the Laplacian signal, which is defined as:

$$\frac{\partial^2 \phi}{\partial x^2} + \frac{\partial^2 \phi}{\partial y^2} = \frac{-4\pi}{\epsilon} \rho_{projected}$$

where $\phi(x,y)$ is the body surface potential, $\rho_{projected}$ is the summed charge density of cardiac sources distant from the surface, and $\epsilon$ is the permittivity of the body considered as a volume conductor. See R. Plonsey, "Laws governing current flow in the volume conductor", in *The Theoretical Basis of Electrocardiography*, C. V. Nelson and D. B. Geselowitz Eds., Clarendon Press, Oxford pp. 165–174, 1976, which is incorporated by reference. For a multi-segment electrode having four exterior segments, the localized ECG signal ($S_L$) is produced as:

$$S_L = S_C - (S_{E1} + S_{E2} + S_{E3} + S_{E4})/4,$$

where $S_C$ is the signal produced by the center segment and $S_{E1}$, $S_{E2}$, $S_{E3}$ and $S_{E4}$ are the signals produced by the exterior segments.

After the localized ECG signals are produced, the signal-to-noise ratios of the signals are enhanced (step 520). A localized ECG signal may be modelled as:

$$x(t) = s(t) + n(t),$$

where $x(t)$ is the ECG signal, $s(t)$ is the cardiac signal component, and $n(t)$ is noise. In general, a signal is present in the localized ECG signal in proportion to the fourth power of the reciprocal of the distance from the source of the signal to the electrode on the body surface. Thus, the strength of the cardiac signal components $s(t)$ is proportional to the fourth power of the reciprocal of the distance from the heart to the electrode. Since sources of electrical activity, such as chest muscles, that conflict with measurement of cardiac activity are much closer to the body surface than the heart, cardiac signals constitute only a small portion of the localized ECG signal. By contrast, since signals are present in a standard ECG signal in proportion to the square of the reciprocal of the distance from the source to the body surface, cardiac signals constitute a larger porion of the standard ECG signal. Thus, the signal-to-noise ratio of the localized ECG is worse than that of the standard ECG. Enhancement of the signal-to-noise ratio may include estimating a representative localized ECG signal, or representative beat, during intervals or stages of the stress test. Other implementations may use different localized ECGs. In a general sense, a localized ECG may be viewed as a spatially-high-pass-filtered body surface potential.

Figure 11A:
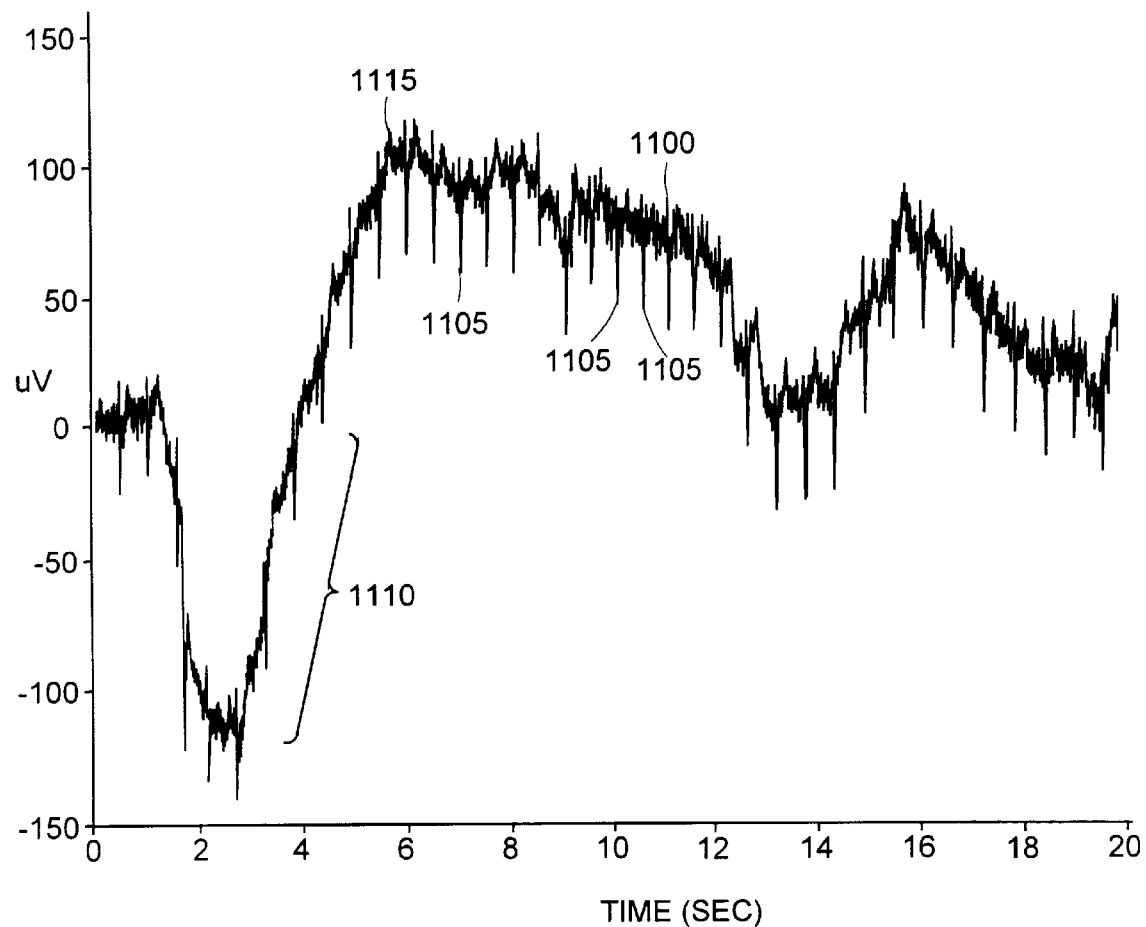
FIGS. 11A and 11B are schematic representations of, respectively, a localized ECG signal and a representative beat of the localized ECG signal.
Figure 11B:
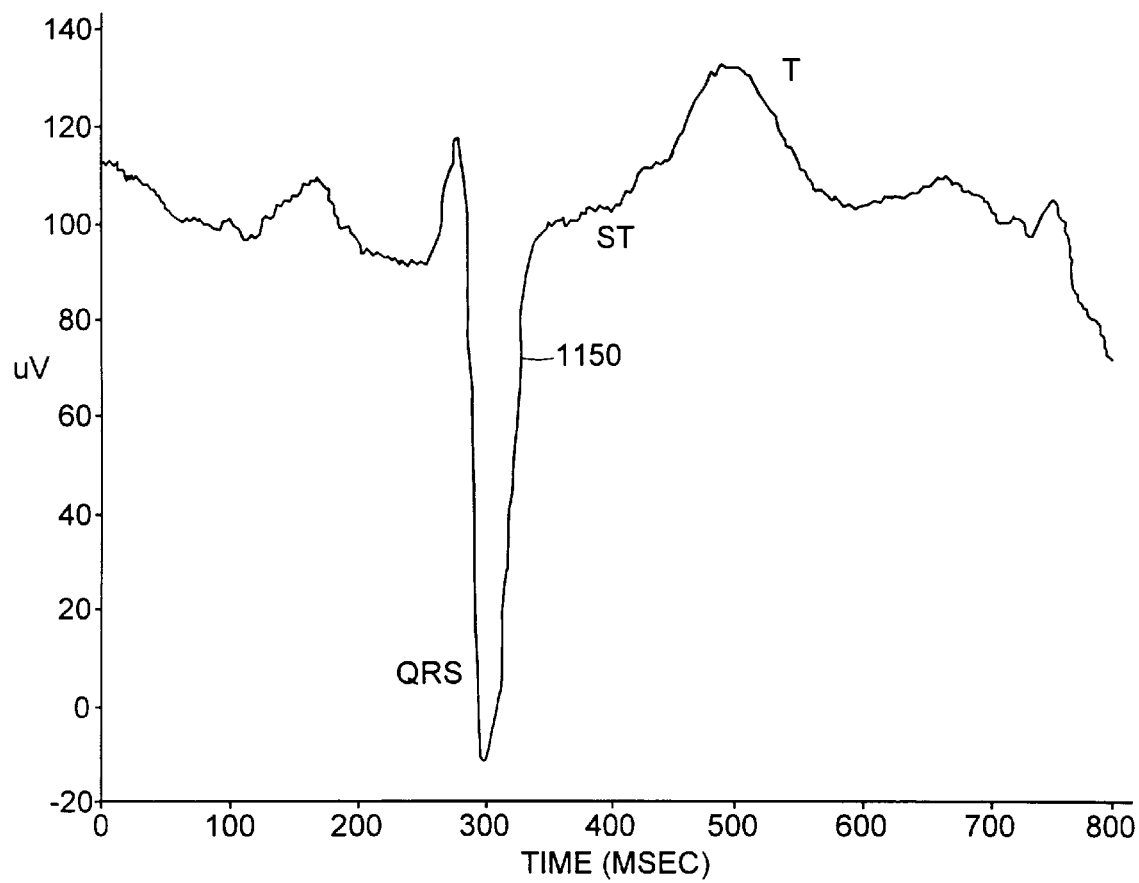

In general, noise in an ECG signal has a low frequency component, referred to as baseline wander, and a high frequency component. For example, FIG. 11A shows a 20-second continuous recording of a localized ECG signal 1100. Each beat of the localized ECG signal may be identified by a QRS complex 1105 of the beat. The signal includes low frequency baseline wander 1110 and high frequency noise 1115. As noted above, the effects of baseline wander are removed by processing the signal using impedance measures. The high frequency noise may be attributable to chest muscle activity, nervous system activity, and electronic instrumentation. The effects of high frequency noise are reduced by computing a representative beat. A representative beat 1150 of the localized ECG signal 1100 is shown in FIG. 11B.

Figure 12:
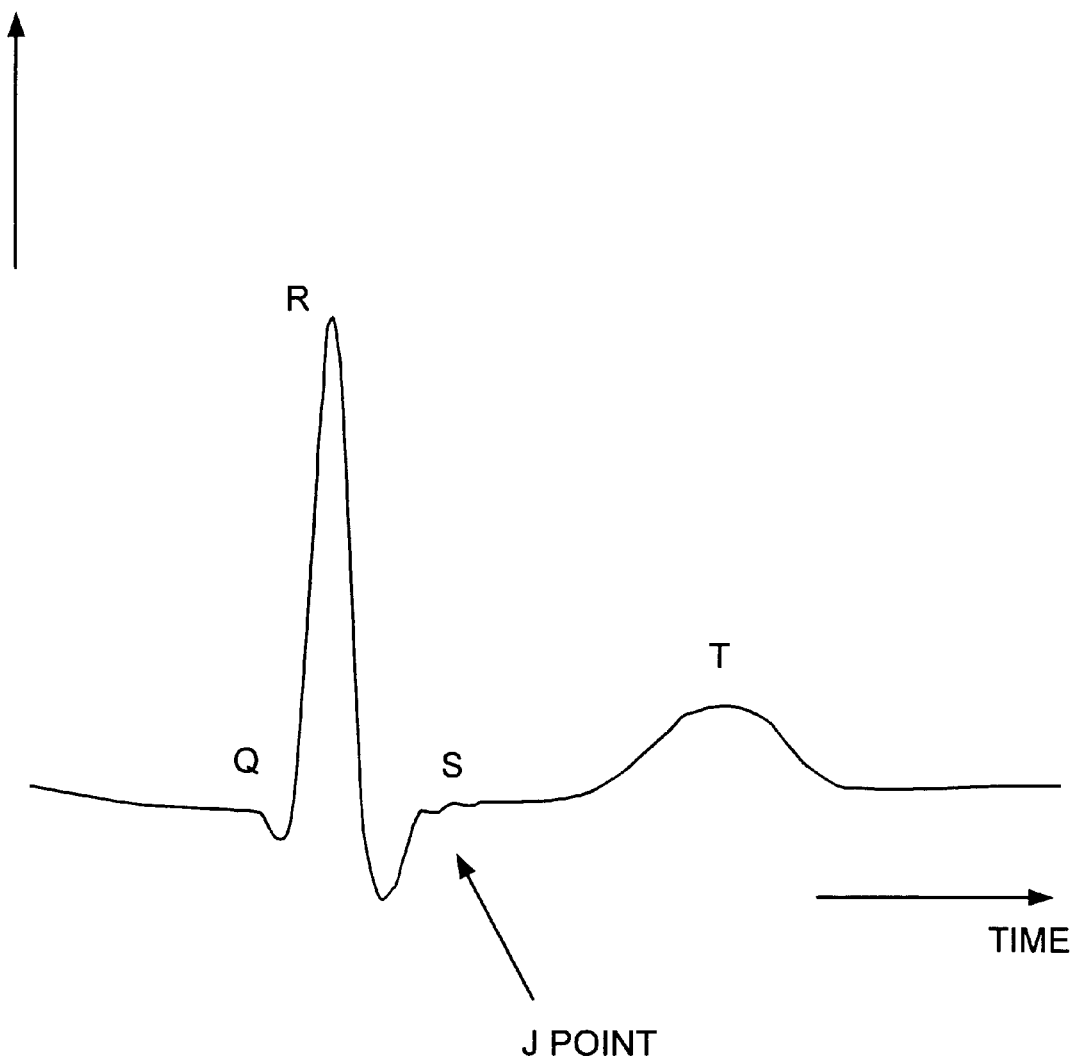
FIG. 12 is a schematic representation of an ECG waveform.

The signal-to-noise ratio is enhanced by computing a measure of statistical central tendency for an ensemble of beats. For example, in one approach, a median beat is computed for the ensemble of beats. With reference to the ECG waveform of FIG. 12, the beats of the ensemble are time-aligned by determining fiducial points of the QRS complex of each beat and aligning the beats relative to the fiducial points. For each time sample, corresponding values for the ensemble of beats are ranked according to their magnitudes. The median beat is then computed by selecting the median value for each time increment. A signal-to-noise-ratio-enhanced ECG waveform x'(t) composed of median beats produced in this manner is substituted for the ECG waveform x(t) in subsequent processing.

The median beat may be computed using a moving-average procedure in which the oldest beat is dropped from the ensemble when a new beat is added. This procedure ensures that sudden changes in the ECG waveform resulting from, for example, increases in noise do not distort the median beats that comprise the noise-reduced waveform. The median beats may be further immunized from corruption due to noise by limiting the change in the value of a time sample between median beats to a maximum value, such as, for example, 10 $\mu$V. The median beat computation is useful when the initial signal-to-noise ratio is poor and there are only a small number of beats available for processing.

An alternative approach to enhancing the signal-to-noise ratio is to perform ensemble averaging of the available beats. For an ensemble of I time-aligned beats, the ensemble average, $x_A'(t)$, is given by:

$$x_A'(t) = \sum_{i=1}^{I} \frac{x_i(t)}{I} = s(t) + \frac{n_A'(t)}{\sqrt{I}},$$

where the subscript i refers to the beat number in the ensemble (1 to I), s(t) is the repetitive cardiac signal, and $n_A'(t)$ is the noise of a typical beat, assuming that the noise has a Gaussian distribution across the ensemble and is uncorrelated with the cardiac signal. See P. Lander et al., "Principles and Signal Processing Techniques of the High Resolution Electrocardiogram", Prog. Cardiovasc. Dis. 35(3):169–188, 1992, which is incorporated by reference. The averaging process attenuates the noise in a statistically predictable fashion, without affecting the cardiac signal component.

Ensemble averaging produces a good unbiased estimate of the cardiac signal component. An enhancement of this approach is to reject extremely noisy beats from the ensemble average on the basis of signal variance measurements. See P. Lander et al., "Principles and Signal Processing Techniques of the High Resolution Electrocardiogram", Prog. Cardiovasc. Dis. 35(3):169–188, 1992. As also noted in that reference, another enhancement is to apply an a posteriori Wiener filter to the ensemble average to improve the mean-squared error of the cardiac signal estimate.

Next, the localized ECG signals are normalized (step 525). (Normalization also may be performed before the signal-to-noise ratios of the ECG signals are enhanced.) With reference to the ECG waveform of FIG. 12, an ST segment change of more than 100 $\mu$V in the standard ECG is conventionally considered to be indicative of myocardial ischemia. In the localized ECG, the scale of the signal is altered due to the process of computing an approximation to the Laplacian. For this reason, the normalization step adjusts the scale of the localized ECG signal to obtain a uniform measurement of ST segment change that can be related to myocardial ischemia. Normalization is achieved by multiplying the ECG waveform by a normalization, or scaling, function. This results in localized ECG signals that are comparable to each other, either between different locations on the body surface or between different patients.

In a first method of normalization, the localized ECG signals are scaled by the maximum peak-to-peak value of the QRS complex (see FIG. 12) at the center segment of the corresponding multi-segment electrode. Other suitable scale factors include amplitudes recorded from the QRS complex or the T wave, or from the ECG value anywhere within the ST segment. The scale function also may be derived from a bipolar ECG, multipolar ECG, or the Laplacian ECG itself. An alternative approach is to scale all localized ECGs from one patient with a single value recorded from the set of unipolar, multipolar, or Laplacian ECGs recorded from the body surface of that patient. For example, this value may be the maximum value of the peak-to-peak amplitude of the QRS complex for any electrode segment, or the maximum value of the ST segment of the ECG for any electrode segment.

Referring again to FIG. 9, once the localized ECG signals have been generated (step 415), the processor measures parameters from the localized ECG signals (step 420). The parameters measured may be variations in the amplitude of the ST segment (FIG. 12) at, for example, the J point, 60 milliseconds after the J point, or at either of these points after subtracting the value of the ECG signal at the onset of the QRS complex. The J point is the point defining the end of the QRS complex. The J point may be identified as the point where the slope of the S wave changes gradient sufficiently to be considered part of the ST segment rather than part of the QRS complex. This may be done, for example, by identifying a significant change in the absolute spatial velocity vector, computed from up to three orthogonal leads, working backwards from within the ST segment into the QRS complex. This process is discussed, for example, by M L Simoons et al. in "Online Processing of Orthogonal Exercise Electrocardiograms", Computers and Biomedical Research 8:105–117, 1975, which is incorporated by reference. Other parameters that could be measured include the value of the ECG waveform at other points in the ST segment, the slope of the ST segment, a parameter of the T wave, such as the maximum value or the duration of the T wave, or a parameter of the QRS complex, such as the duration of the QRS complex.

The parameters may be measured after reconstructing a conventional twelve-lead ECG from the set of localized ECGs by transformation of at least three localized or unipolar ECG signals. A localized twelve-lead ECG also may be constructed using Laplacian signals recorded at the conventional electrode sites or a transformed set recorded elsewhere. The transformed set may be obtained by combining unipolar or localized ECGs sensed at points on the body surface, either at the sites of the conventional twelve-lead ECG or elsewhere.

Parameter values may be computed once during each of a series of epochs, where the epochs may be user-selected, automatically determined, or pre-defined. For example, when the epochs are the stages of the stress test and the period following the stress test, one parameter value may be computed for each localized ECG signal in each epoch. The epochs also may be defined as having substantially equal, fixed durations, that may or may not overlap. Similarly, the epochs may be defined as each containing approximately the same number of beats, or as containing a representative beat with a signal-to-noise ratio that equals the signal-to-noise ratio of representative beats of other epochs.

Once parameter values have been measured from the array of localized ECG signals (step 420), the parameter values are arranged in an array with coordinates corresponding approximately to the electrode sites (step 425) and a gridding procedure is applied to the array (step 430). In some cases, the original array of parameter values is non-uniform. The gridding procedure includes interpolation of the parameter values to a more dense, uniform grid of which the parameter values are nodes. Missing values can occur because of the absence of one or more recording electrodes, due to restraints on applying electrodes to the patient, electrode failure, noisy ECG waveforms or other difficulties in obtaining a reliable measurement of the parameter value from each electrode. Interpolation is used to fill in missing values in the array.

An alternative method of gridding parameter values measured from the localized ECG signals is referred to as kriging. Kriging is a technique developed in geostatistical analysis. See J. C. Davis, *Statistics and Data Analysis in Geology*, 2nd Edition (1986). Kriging includes separately estimating the grid for local and global elements of the original array of parameter values. In this context, "local" refers to rapidly changing or transient activity present in only a portion of the map. "Global" refers to features of the parameter distribution that are either slowly changing, or essentially unchanged, and present in the majority of the map.

The gridding procedure also may include steps to enhance the accuracy of the grid. For example, the interpolated grid may be smoothed by convolution with a two-dimensional function that is equivalent to a lowpass filter. Further smoothing of the grid may be performed to accentuate its global or spatially consistent patterns. For example, small regions of false positivity or abnormalcy may be removed, as such regions could be artifacts of the interpolation process. Similarly, spatial differentiation can be used to highlight local changes in the grid. For example, small regions in the map where the localized measures of myocardial ischemia have a particular state, such as ST segment changes greater than 100 $\mu V$, may be delineated. Noncontiguous activity on the body surface can be identified by estimating local variance in the grid. This is a process commonly referred to as edge detection in image processing. Use of edge detection permits the identification of regionalized changes in the cardiac source distribution, signalled by relatively abrupt changes in the differential of the body surface potential.

The grid may be displayed as a map of isopotential, isochronous, or other isometric quantities (step 435). The map is produced to transform the uniform grid, which is a mathematical representation of the ECG data, to a graphical representation that may be evaluated visually. Contouring, as described by J. C. Davis in *Statistics and Data Analysis in Geology*, may be used to generate a contour map or a solid color map. The map may include contours, polar images (color maps), and gray scales. Superimposed on the map may be a number of markers useful in interpreting the localized measure of ischemia. These include markers denoting electrode positions, and localized or conventional ECG waveforms, placed over the map at their recording sites. The map further includes demarcation of areas of missing values. The map may be displayed as a two-dimensional surface where the anterior, lateral and posterior portions of the map are laid out in a two-dimensional projection. Alternatively, the map may be displayed as a three-dimensional surface, representing the anterior, lateral and posterior elements of the body surface. The map may further include separate two-dimensional representations of portions of the body surface.

Figure 13A:
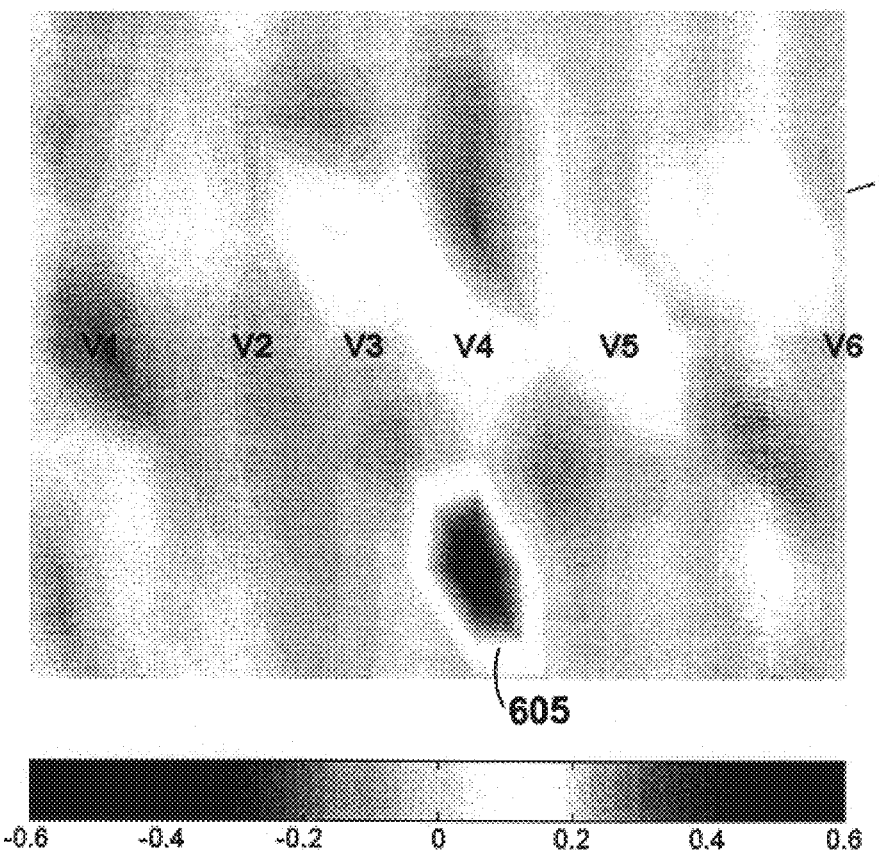
FIG. 13A is an image of the Laplacian of a body surface distribution, showing an isopotential map of ST segment changes computed from localized ECG recordings.
Figure 13B:
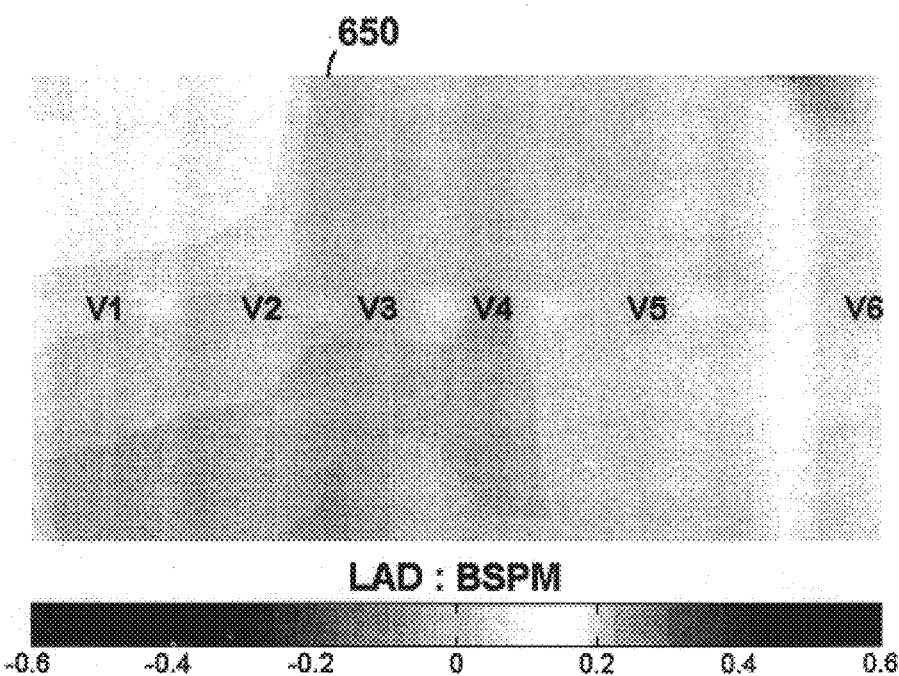
FIG. 13B is an image of a body surface potential distribution, showing an isopotential map of ST segment changes computed from conventional, unipolar ECG recordings.

FIG. 13A shows an isometric map 600 computed from values of ST segment change measured from an array of localized ECG signals. This is a map of the surface Laplacian, i.e., the spatial differential of the body surface potential distribution. FIG. 13A shows distinct areas of abnormal ST segment change, indicated by the darker shaded areas 605. These areas are localized and the map itself has a noncontiguous character, with ST segment changes occurring locally. By contrast, FIG. 13B illustrates an isopotential map 650, computed from values of ST segment changes measured from an array of unipolar ECG signals. This is a body surface map of the surface potential distribution. There are no areas of significant (i.e., greater than 100 $\mu V$) ST segment change and the map has a smooth appearance, indicating a smooth and gradual change in parameter values within the array of conventional, unipolar ECG signals. The distinction between FIGS. 13A and 13B illustrates the power of the illustrated approach to identify and characterize a localized measure of myocardial ischemia at the body surface.

Figure 14:
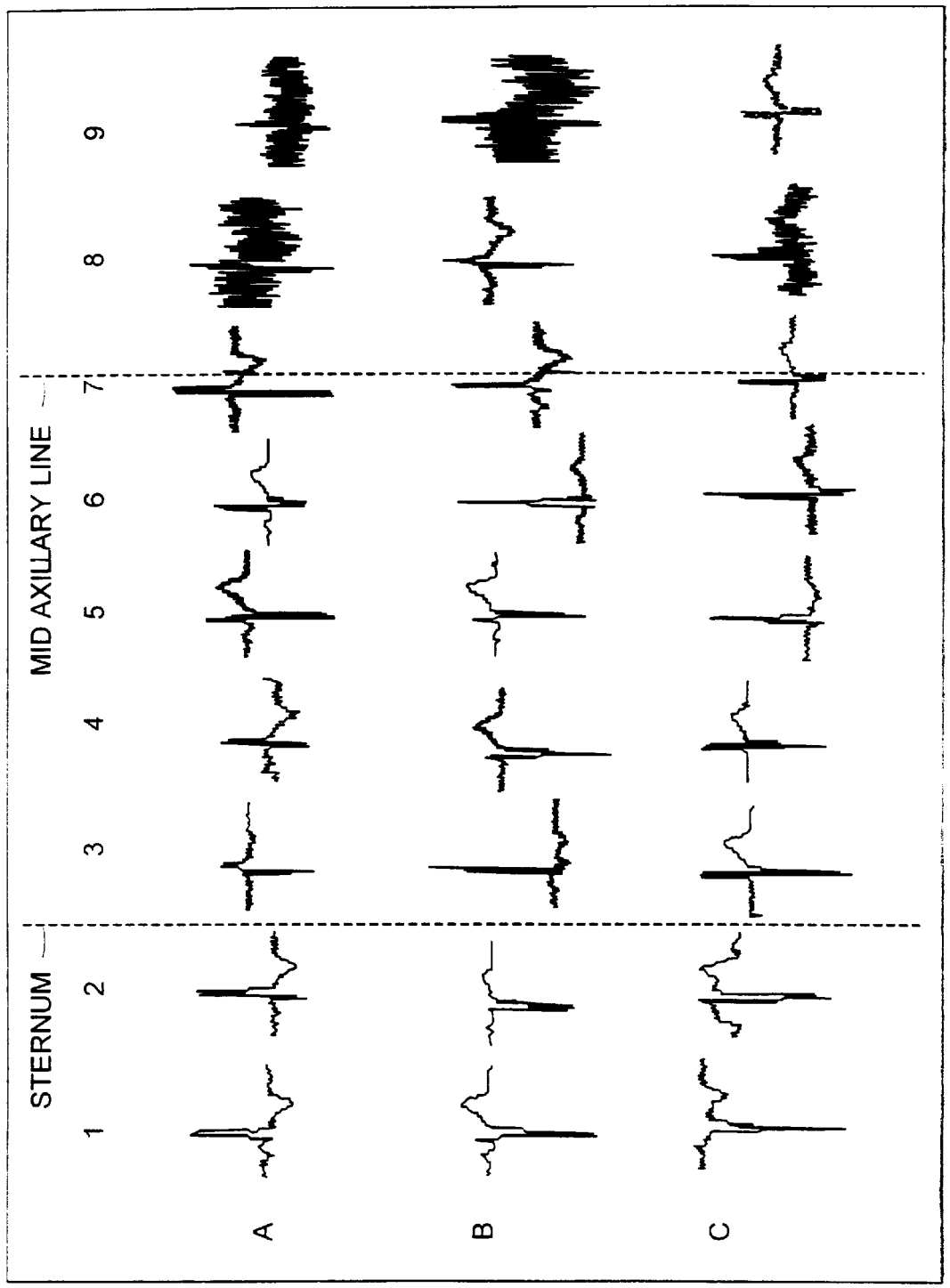
FIGS. 14 and 15 are screen displays of the system of FIG. 1.
Figure 15:
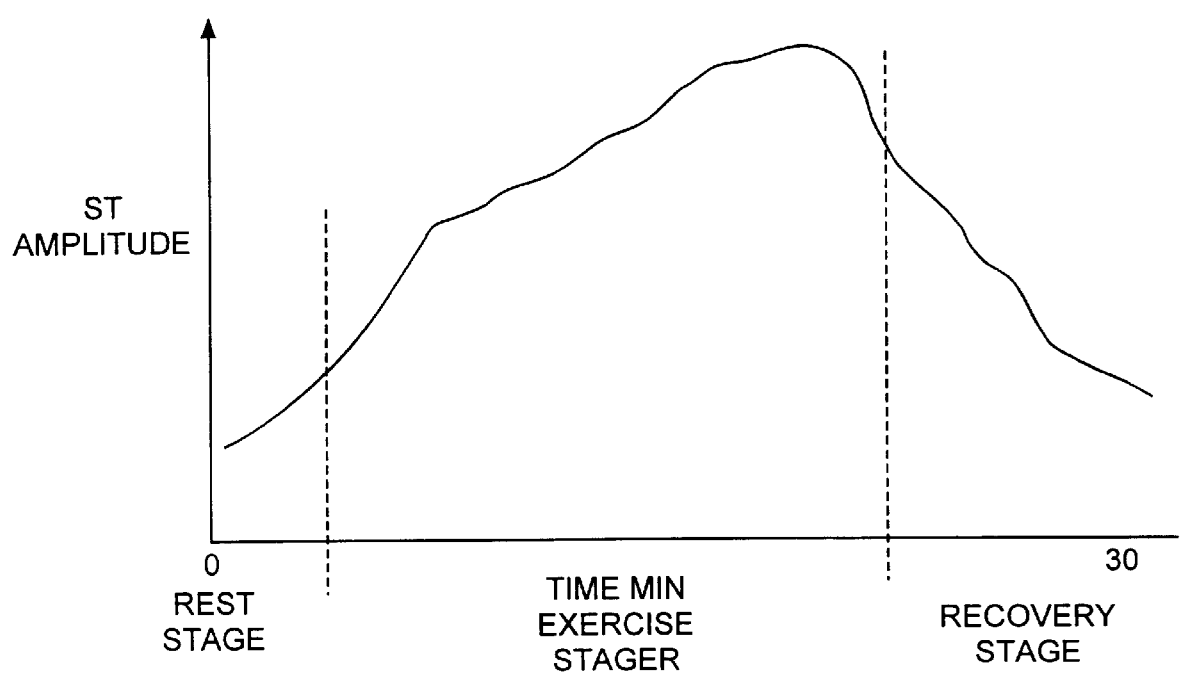

Other information may be displayed. For example, an array of localized ECG waveforms may be displayed in a grid format, with the position of each ECG waveform corresponding to the coordinates of the multi-segment electrode that recorded the waveform. For example, FIG. 14 presents an array of localized ECG waveforms by showing the anterior, lateral, and posterior regions of the body as a two-dimensional flat surface. Dotted lines show the line of the sternum (the center of the body) and the left mid-axiliary line (the left side of the body). The display also may include an outline of the torso with the ECG waveforms superimposed. In another format, the display may be a composite image, with anterior, lateral and posterior portions of the electrode array shown in approximate physical relation to each other, either in a two-dimensional projection or a three-dimensional display. The display also may include color coding of portions of the ECG waveforms to represent their amplitude, state (normal or abnormal), and/or their assessed relation to myocardial ischemia, as indicated by associated parameters measured as described above. As shown in FIG. 15, a graphical display of trends of the localized measure obtained from the localized ECG waveforms (such as ST segment change) also may be displayed. Parameters from the localized ECG are shown in a time-varying trend display, with one parameter computed at an interval of one heart beat or greater. As shown, the display also may identify stages of an associated stress test. The trend display may be color-coded to represent normal or abnormal states or assessed relations of the ECG waveforms to myocardial ischemia.

As noted above, the system 100 may be used to monitor a subject suspected of experiencing a myocardial infarction. When the system 100 is used in this manner, the processor 130 does not need to control physiologic stress of the subject's heart, and the optional lead 150 for controlling an exercise device need not be included. Instead, the processor monitors the subject's cardiac activity over an extended period (e.g., one to six hours) and compares the cardiac activity from regular intervals of that activity to identify trends indicative of myocardial infarction.

Figure 16:
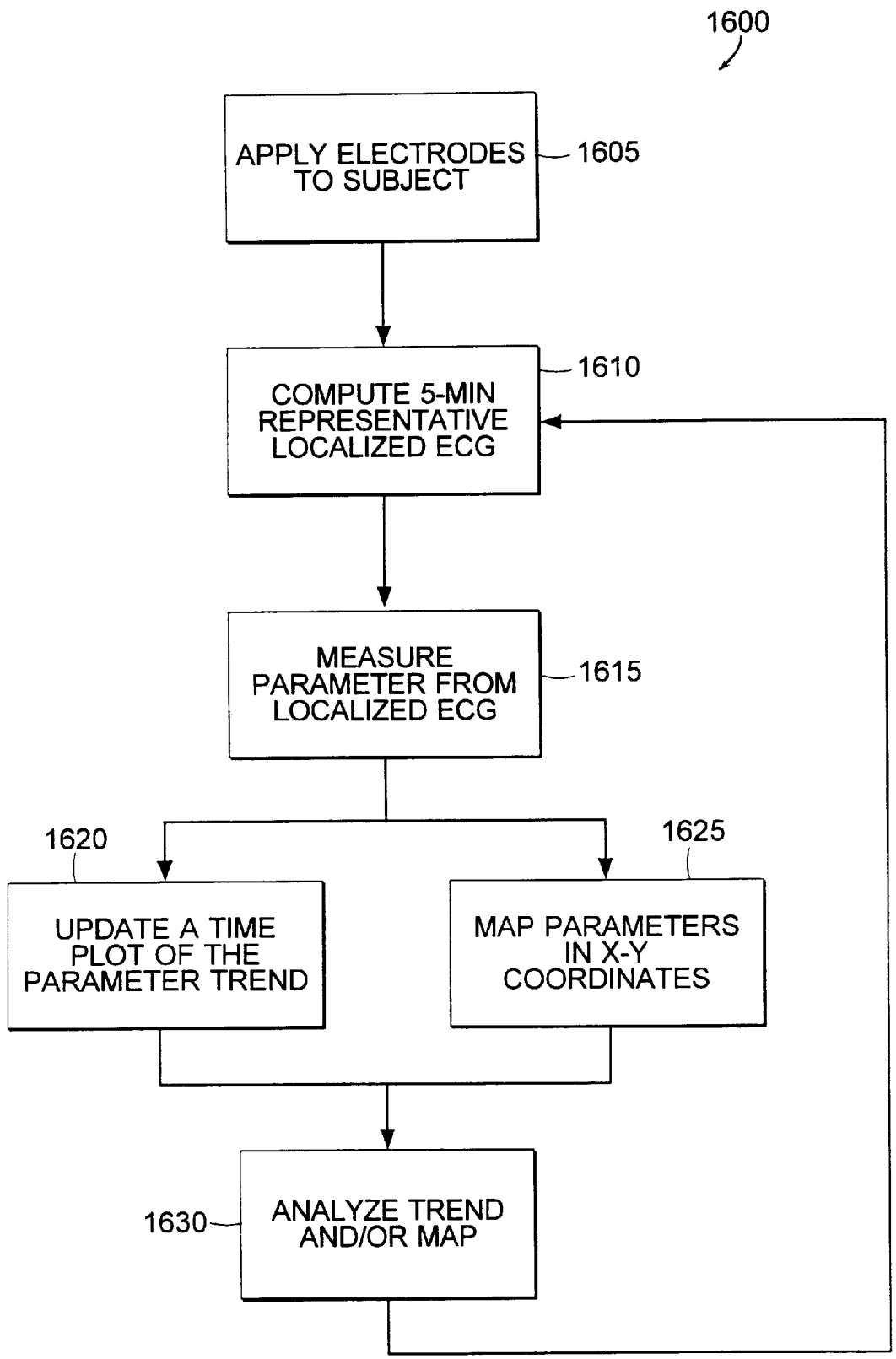
FIG. 16 is a flow chart of a procedure for monitoring a subject expected of experiencing a myocardial infarction.

The system 100 may be used to monitor a subject suspected of experiencing a myocardial infarction according to the procedure 1600 illustrated in FIG. 16. Initially, the electrodes are applied to the subject's torso (step 1605). As with monitoring for myocardial ischemia, coverage of the electrodes extends vertically from just below the clavicle to the bottom of the rib cage and horizontally from the anterior right mid-clavicular line to the posterior left mid-clavicular line. The electrodes may be applied as individual electrodes 200 (FIG. 2) or as a belt of electrodes 300 (FIG. 8).

Once the electrodes have been applied to the subject's torso, a representative, localized ECG is generated for a five minute interval of signals from the electrodes (step 1610). The localized ECG is generated using the techniques described above with reference to FIG. 10.

Next, a parameter of the localized ECG is measured (step 1615). Suitable parameters include, but are not limited to, the magnitudes, shapes, or durations of the ST segment, the QRS complex, or the T wave. The measured parameter is used to update a time plot of a parameter trend (step 1620) that may be displayed on the display 135. For example, if the measured parameter is the amplitude of the ST segment, the system could provide a display similar to that of FIG. 15. The display of the measured parameter also may be provided in conjunction with a display of the localized ECG signal. The system attempts to track the underlying state of the heart. There is no a priori known 'normal' state. As such, the system is employed to identify an evolving pattern of changes indicative of myocardial infarction as a final state, to be detected as early as possible. By updating the time plot frequently (e.g., every five minutes), the system provides timely information for use in identifying this evolving pattern to assess and monitor the subject's condition.

The time plot may have previously-determined fixed bounds for normal variation. For example, an abnormal ST segment change might be defined as an ST segment change greater than 100 $\mu$V. Such a change may be plotted in a different color for use as a guide to changes in underlying cardiac activity, or may be used to activate, for example, an audible alarm. The time plot may be annotated with markers to indicate the time of symptoms or other events (e.g., chest pain) or the start of therapy (e.g., thrombolysis).

When localized ECG signals are obtained for multiple locations on the patient's body, additional diagnostic information may be included in the parameter trend display by mapping the localized ECG signals in X–Y coordinates on the display 135 (step 1625). For example, the values of parameters for multiple locations may be shown in a map plotted on coordinates matching the electrode positions on the body. Time trends may be presented by displaying a sequence of such maps, or by mapping changes in the parameters over time at different locations. The maps identify areas of the body where changes in cardiac activity are registered. The areas of the body can be associated with each of the three major arteries: the LAD (Left Anterior Descending), the LCX (left circumflex artery), and the RCA (Right Coronary Artery). This permits the map to be used to identify the blocked artery or arteries.

Figure 17:
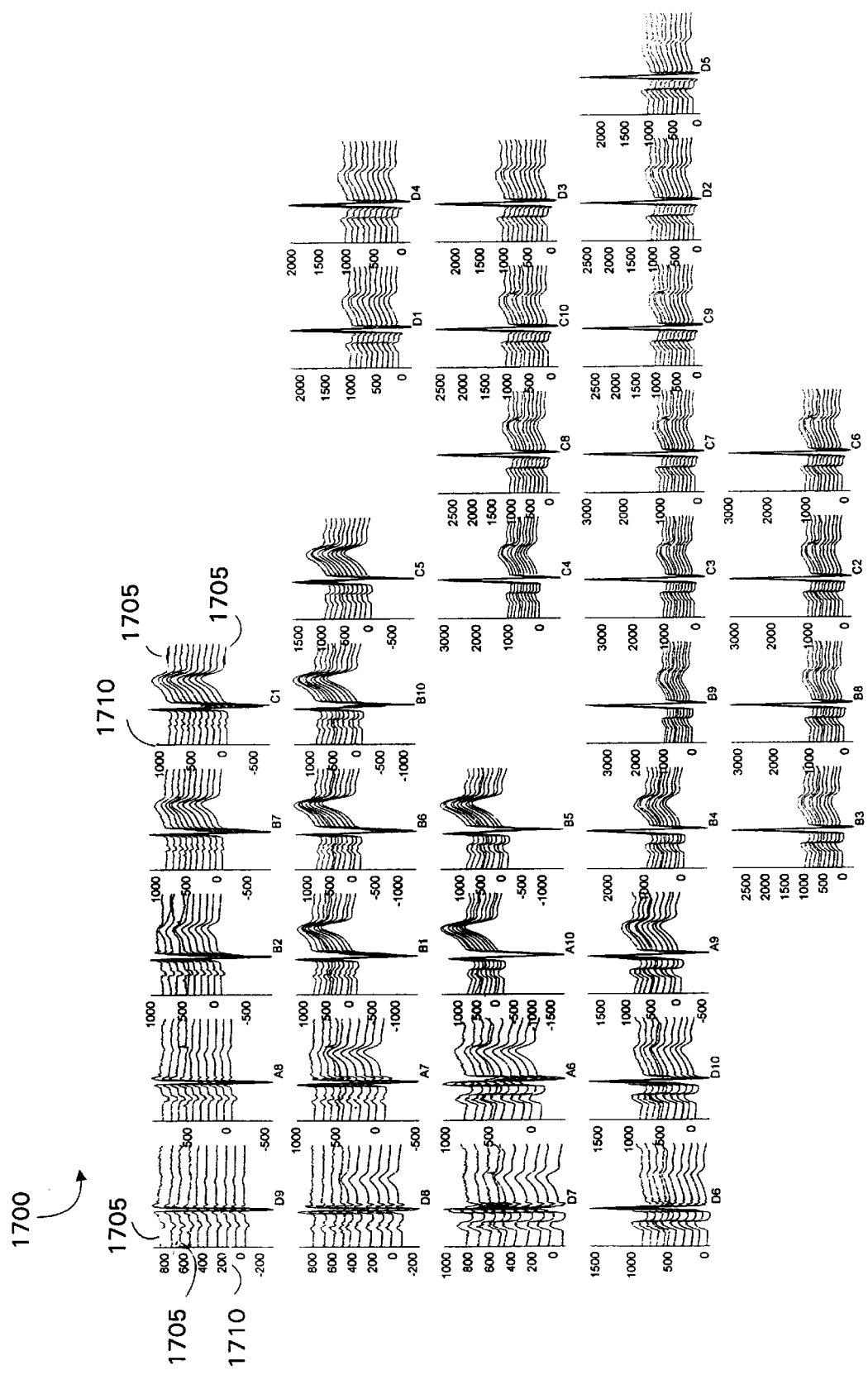
FIGS. 17–19 are screen displays of the system of FIG. 1.
Figure 18:
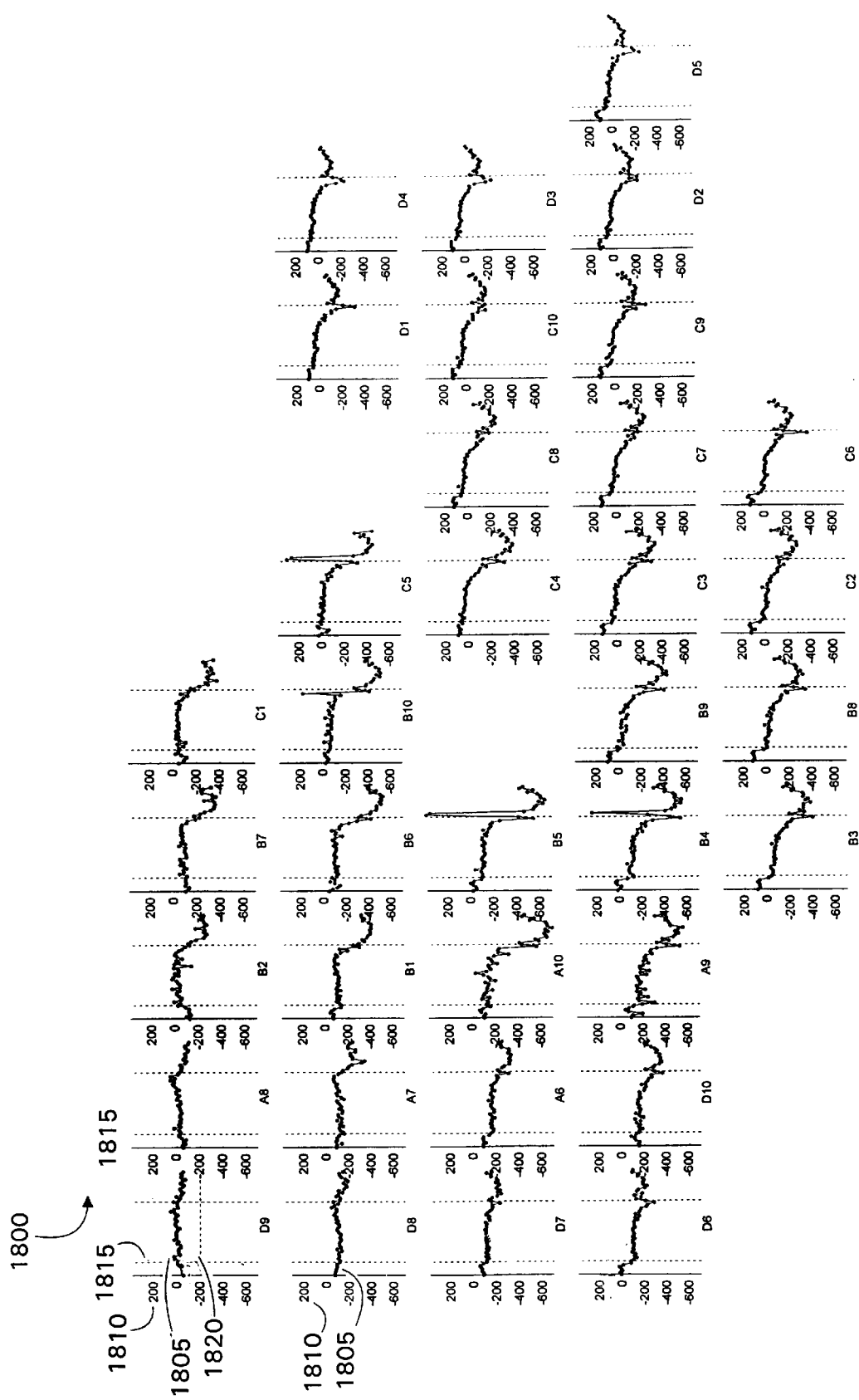
Figure 19:
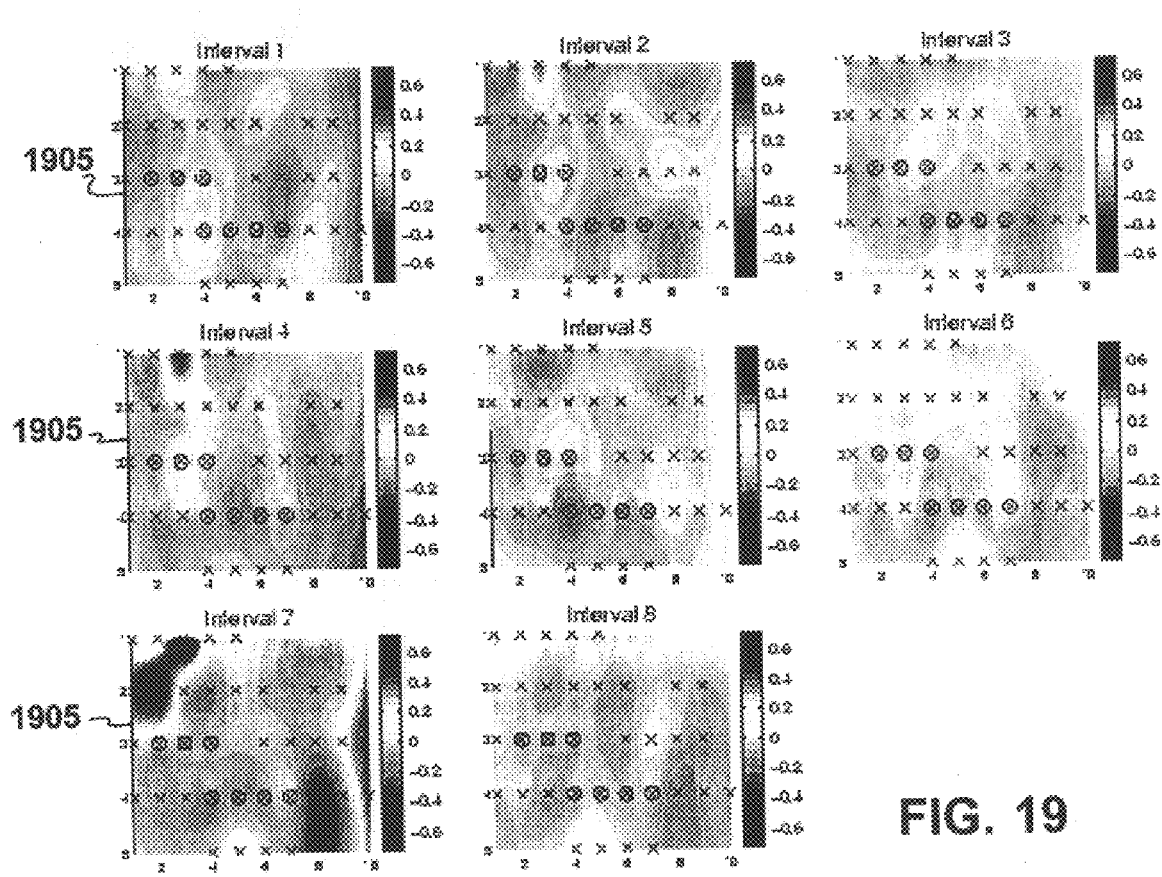

FIGS. 17–19 illustrate examples of maps that may be provided by the system 100. FIG. 17 illustrates a representative beat map 1700 in which the beats are presented in a stacked format. The waveforms 1705 in each panel 1710 are representative beats computed for successive five minute intervals. This format permits a ready assessment of subtle changes in ECG shape and allows one to track the progression of the shape over periods of time. The duration of the representative beat calculation is a trade-off between greater noise reduction (longer times) and an ability to track rapid changes (shorter times). The arrangement of ECG waveforms in a grid mirrors the positions of the recording electrodes on the body surface.

Instead of mapping the representative beats themselves, it may be preferable to monitor a single parameter computed from each representative beat. FIG. 18 shows a body surface distribution 1800 of a single parameter 1805 (the value of the J point of the ECG) over a 30-minute time period. Each panel 1810 of the display represents one of the electrodes. As shown, there is a trend towards progressively greater depression of the ST segment in the ECG with time. There is also a tendency for the changes to be larger on the left and lower portions of the body.

The dotted lines 1815 may represent annotated events, such as the onset of chest pain or the start of thrombolytic therapy. A horizontal line 1820 may be drawn on the tracings to denote a threshold value for the parameter to be considered abnormal. For example, if the J point value goes below –200 $\mu$V, it might be considered abnormal. The body surface distribution illustrates representative beats that were computed every thirty seconds, instead of every five minutes, as discussed above.

The display 1900 of FIG. 19 provides a sequence of eight maps 1905, computed in successive five-minute intervals. Each map represents the J point value as an interpolated regional variable. The crosses 1910 represent recording electrode positions, with the circled crosses 1915 representing the standard ECG precordial sites. The maps show significant regional changes in interval 8.

The displayed time trend and, when available, the map may be analyzed to detect a myocardial infarction (step 1630). The process is repeated by generating a localized ECG signal for the next five minute interval of the signals from the electrodes (step 1610). The time plot may be updated at regular intervals (e.g., every five minutes), or new points may be added to the time plot only when a significant change occurs in the monitored parameter (e.g., an ST segment change greater than 100 $\mu$V). The criteria for what constitutes a significant change may be predetermined (i.e., universally applicable) or patient-specific (i.e., a departure from previously recorded patterns for the patient). Such changes may occur before, progressively (or suddenly) during, and after administration of thrombolytic therapy.

Other embodiments are within the scope of the following claims. A localized ECG signal also may improve the assessment of cardiac electrical stability for the purpose of identifying individuals at risk for life-threatening ventricular arrhythmias. For example, the system 100 may be configured to detect alternans, a subtle beat-to-beat change in the repeating pattern of an ECG waveform, which can be indicative of electrical instability of the heart and increased susceptibility to sudden cardiac death. ECG systems configured to detect alternans are discussed in U.S. application Ser. No. 08/379,375, entitled "MEASURING AND ASSESSING CARDIAC ELECTRICAL STABILITY" and filed Jan. 26, 1995, and U.S. application Ser. No. 08/557,883, entitled "USING RELATED SIGNALS TO REDUCE ECG NOISE" and filed Nov. 14, 1995, both of which are incorporated by reference.

A localized ECG may also improve the assessment of late potentials. Late potentials are microvolt-level signals following normal ventricular depolarization, and originating from localized regions of the ventricle. Late potentials represent slow or delayed conduction from these localized regions. The localized ECG will improve the signal-to-noise ratio of late potentials originating from these localized regions. Thus, by averaging the ECG over many beats and filtering, these small signals can be detected. Late potentials are associated with life-threatening ventricular arrhythmias.

Localized timing may also be used to more accurately measure QT dispersion, which is the maximum difference between the duration of the QT interval of any two regions of the heart. QT dispersion is a measure of dispersion of ventricular recovery and has been linked to susceptibility to serious ventricular arrhythmias. Localized timing may also be useful for detecting delayed conduction in regions of the heart. Delayed conduction often forms the substrate for serious ventricular arrhythmias. Similarly, better localization can also improve the assessment of atrial electrical stability.

A localized ECG may also be used for diagnostic purposes. It can be useful for assessing atrial activity, such as by determining the timing of the P wave, which corresponds to the electrical activation of the atria. The evaluation of cardiac arrhythmias frequently requires the accurate detection of the P wave, which may be obscured by noise or by other ECG features in the standard twelve ECG leads. By using a localized ECG which accentuates the P wave, the localized timing of the atrial activation can be more accurately determined.

The evaluation of a wide complex tachycardia is an important application for detecting the relative timing of the atria and ventricles. A wide complex tachycardia is a rhythm characterized by a high heart rate and beats which are wider than those of normal ECG. The tachycardia may be a ventricular tachycardia, in which the ventricle is repetitively activated at a high rate, either through spontaneous ventricular depolarizations or due to a re-entrant circuit in the ventricle. The beats are wide because they do not propagate using the specialized conduction system of the heart. Ventricular tachycardia is a potentially life threatening rhythmic disturbance. The tachycardia may be a supraventricular tachycardia, in which the beats originate in the atrium or atrio-ventricular node, but the beats are wide because the specialized conduction system does not respond adequately. By knowing the relative timing of the atrial and ventricular activations, a wide complex tachycardia can be more accurately identified as ventricular or supraventricular in origin.

A localized ECG can also be useful for detecting the fetal ECG while minimizing the detection of the maternal ECG.

Other embodiments may use different numbers or types of electrodes. Other embodiments may put more electrodes on the body to localize signals from more regions of the heart. In addition, much of the processing discussed above could be accomplished using groups of single terminal electrodes in place of the multi-segment electrodes. Similarly, the multi-segment electrodes could be modified. For example, different numbers (e.g., 3 or 5) of exterior segments, or segments having different shapes (e.g., arcuate or triangular segments), could be used.

What is claimed is:

1. A method for monitoring a subject suspected of experiencing a myocardial infarction, the method comprising:

applying sensors to the subject, the sensors being configured to produce electrical signals representative of cardiac activity of the subject;

receiving electrical signals from at least two of the sensors;

processing the received signals to obtain a localized electrocardiogram;

creating a localized cardiac measure from the localized electrocardiogram; and analyzing the localized cardiac measure to determine whether the subject is experiencing a myocardial infarction.

2. The method of claim 1, wherein analyzing the localized cardiac measure comprises analyzing a temporal trend in the localized cardiac measure to generate a temporal trend measurement and performing further analysis on the temporal trend measurement.

3. The method of claim 2, further comprising displaying the temporal trend measurement.

4. The method of claim 1 wherein the creating step comprises generating a localized measure of myocardial ischemia as the localized cardiac measure.

5. The method of claim 1 wherein the creating step comprises creating the localized cardiac measure during a specific portion of a cardiac cycle.

6. The method of claim 5 wherein the specific portion of the cardiac cycle comprises the ST segment of the cardiac cycle.

7. The method of claim 6 wherein the localized cardiac measure comprises a measure of ST segment change.

8. The method of claim 6 wherein the creating step includes determining a normalized value of ST segment change.

9. The method of claim 6 wherein the processing step further includes determining characteristics of a body surface spatial distribution of ST segment changes.

10. The method of claim 5 wherein the specific point in the cardiac cycle comprises a QRS complex of the cardiac cycle.

11. The method of claim 10, wherein the localized cardiac measure comprises a measure of an amplitude of the QRS complex.

12. The method of claim 1 further comprising obtaining localized cardiac measures at multiple locations.

13. The method of claim 1 further comprising enhancing a signal-to-noise characteristic of the localized cardiac measure by modifying the localized electrocardiogram.

14. The method of claim 13 wherein the step of enhancing comprises using a measure of statistical central tendency.

15. The method of claim 14, wherein the measure of statistical central tendency comprises an average.

16. The method of claim 14, wherein the measure of statistical central tendency comprises a median.

17. The method of claim 13, wherein modifying the localized electrocardiogram comprises generating a representative beat.

18. The method of claim 17, wherein generating a representative beat comprises rejecting abnormal beats.

19. The method of claim 17, wherein generating a representative beat comprises rejecting beats having a noise level above a predetermined threshold.

20. The method of claim 13, further comprising displaying the modified localized electrocardiogram.

21. The method of claim 13, wherein generating the localized cardiac measure comprises using the modified localized electrocardiogram.

22. The method of claim 1 further comprising normalizing the localized cardiac measure.

23. The method of claim 22, further comprising:
generating a standard electrocardiogram; and
generating a parameter from the standard electrocardiogram;
wherein the step of normalizing includes using the parameter generated from a standard electrocardiogram.

24. The method of claim 23, wherein the parameter comprises an amplitude of a QRS complex of the standard electrocardiogram.

25. The method of claim 22 wherein the step of normalizing includes using a parameter generated from the localized electrocardiogram.

26. The method of claim 25, wherein the parameter comprises an amplitude of a QRS complex of the localized electrocardiogram.

27. The method of claim 1 further comprising processing the received signals to remove baseline noise using an impedance signal estimate.

28. The method of claim 1 wherein the processing step includes reconstruction of a standard electrocardiogram by transformation of the signals received from the sensors.

29. The method of claim 1 further comprising presenting a display of the localized cardiac measure.

30. The method of claim 29 wherein localized cardiac measures are obtained at multiple locations and the display includes a map of the localized cardiac measures at different locations.

31. The method of claim 30 wherein the map comprises a map that uses colors to represent ranges of values of the localized measures.

32. The method of claim 29 wherein localized cardiac measures are obtained at multiple locations and the display includes a graphical representation of the localized measures at positions corresponding to locations of the sensors.

33. The method of claim 29 wherein the display comprises a graphical image with superimposed cardiac measures.

34. The method of claim 1 further comprising displaying a plot of a time-dependence of a quantity derived from the localized cardiac measure.

35. The method of claim 1 further including estimating the localized cardiac measure at locations other than the locations of the received signals.

36. The method of claim 1, further comprising displaying the localized cardiac measure to show a temporal trend in the localized cardiac measure.

37. A system for monitoring a subject suspected of experiencing a myocardial infarction, the system including:
sensors configured to be applied to a subject and to produce electrical signals representative of cardiac activity of the subject;
means for receiving electrical signals from at least two of the sensors;
means for processing the received signals to obtain a localized electrocardiogram;
means for creating a localized cardiac measure from the localized electrocardiogram; and
means for analyzing the localized cardiac measure to determine whether the subject is experiencing a myocardial infarction.

* * * * *